(12) United States Patent
Kim et al.

(10) Patent No.: US 12,274,859 B2
(45) Date of Patent: Apr. 15, 2025

(54) DRUG DELIVERY DEVICE AND MANUFACTURING METHOD THEREOF

(71) Applicant: DAEGU GYEONGBUK INSTITUTE OF SCIENCE AND TECHNOLOGY, Daegu (KR)

(72) Inventors: So Hee Kim, Daegu (KR); Hyun Min Moon, Daegu (KR); Nam Sun Chou, Seoul (KR)

(73) Assignee: DAEGU GYEONGBUK INSTITUE OF SCIENCE AND TECHNOLOGY, Daegu (KR)

( * ) Notice: Subject to any disclaimer, the term of this patent is extended or adjusted under 35 U.S.C. 154(b) by 695 days.

(21) Appl. No.: 16/763,872

(22) PCT Filed: Nov. 12, 2018

(86) PCT No.: PCT/KR2018/013721
§ 371 (c)(1),
(2) Date: May 13, 2020

(87) PCT Pub. No.: WO2019/093842
PCT Pub. Date: May 16, 2019

(65) Prior Publication Data
US 2020/0353162 A1    Nov. 12, 2020

(30) Foreign Application Priority Data
Nov. 13, 2017    (KR) .......................... 10-2017-0150689

(51) Int. Cl.
*A61M 5/142*    (2006.01)
*A61B 5/24*    (2021.01)
(Continued)

(52) U.S. Cl.
CPC ........... *A61M 5/14276* (2013.01); *A61B 5/24* (2021.01); *A61M 5/1408* (2013.01); *B05D 1/005* (2013.01);
(Continued)

(58) Field of Classification Search
CPC ............ A61M 5/14276; A61M 5/1408; A61M 2205/0216; A61M 2205/054; A61M 2205/3327; A61M 2205/50
See application file for complete search history.

(56) References Cited

U.S. PATENT DOCUMENTS 6,471,689 B1 * 10/2002 Joseph ................ A61M 5/1723
424/424
7,813,811 B2 * 10/2010 Wingeier ............. A61N 1/0529
607/116

FOREIGN PATENT DOCUMENTS

KR         10-1044661 B1    6/2011
KR    10-2012-0032521 A    4/2012
(Continued)

OTHER PUBLICATIONS

Ryu, Wonhyoung et al., "Biodegradable Micro-osmotic Pump for Long-term and Controlled Release of Basic Fibroblast Growth Factor, Journal of Controlled Release", 2007, vol. 124, pp. 98-105.
(Continued)

*Primary Examiner* — Bradley J Osinski
(74) *Attorney, Agent, or Firm* — LEX IP MEISTER, PLLC

(57) ABSTRACT

A drug delivery device and a method for manufacturing the same, and more specifically, a drug delivery device that can deliver a drug to a biological tissue while minimizing damage thereto and can come into close contact with the biological tissue to be able to measure an electrical signal of or apply electrical stimulation to the biological tissue and a method for manufacturing the drug delivery device are
(Continued)

proposed. The drug delivery device includes a substrate unit that is inserted into a human body and has a porous insertion portion having one or more discharge voids. The insertion portion is provided to be deformable to match a shape of a biological tissue while expanding and contracting as a drug is injected into and discharged from an inside of the injection portion.

7 Claims, 21 Drawing Sheets

(51) Int. Cl.
  *A61M 5/14* (2006.01)
  *B05D 1/00* (2006.01)
  *B05D 3/14* (2006.01)
(52) U.S. Cl.
  CPC ..... *B05D 3/148* (2013.01); *A61M 2205/0216* (2013.01); *A61M 2205/054* (2013.01); *A61M 2205/3327* (2013.01); *A61M 2205/50* (2013.01); *A61M 2207/00* (2013.01)

(56) References Cited

FOREIGN PATENT DOCUMENTS

KR  10-2015-0038895 A  4/2015
KR      10-1824246 B1  1/2018

OTHER PUBLICATIONS

Zhang, L. et al., "Parylene C-mediated-PDMS: an Approach for Functionalization of PDMS Microfuidic Devices", 17th International Conference on Miniaturized Systems for Chemistry and Life Sciences, 2013, pp. 1427-1429, Freiburg, Germany.

* cited by examiner

DRUG DELIVERY DEVICE AND MANUFACTURING METHOD THEREOF

TECHNICAL FIELD

The present invention relates to a drug delivery device and a method for manufacturing method thereof, and more specifically, to a drug delivery device and a method for manufacturing the drug delivery device that is fixable to a biological tissue while minimizing damage thereto, can come into close contact with the biological tissue to directly deliver a drug thereto, and is economical as an additional drug storage is not needed.

BACKGROUND ART

A drug delivery device in the related art uses an invasive device having a substrate made of hard silicone, and thus a biological tissue is damaged in a process of fixing and attaching the invasive device to the biological tissue.

In addition, the drug delivery device in the related art includes an invasive device that penetrates a biological tissue and an additional drug storage that is connected to the invasive device, stores a drug, and delivers the drug to the invasive device. Thus, it is inconvenient to perform processes of producing and assembling the drug delivery device.

In order to solve such a problem, a drug delivery device in the related art using a biodegradable hydrogel matrix is able to store a drug; however, problems arise in that a storing amount of drug is limited and it is difficult to adjust a drug delivery rate.

Besides, the invasive device of the drug delivery device in the related art is not deformed to flexibly match various curves of a biological tissue, thus not coming into close contact with the biological tissue, and thereby it is difficult to inject a drug to a desired position by an accurate dose.

Consequently, it is necessary to provide a drug delivery device that can come into close contact with a biological tissue to accurately inject a drug and does not damage the biological tissue even when being fixed to the biological tissue such that long-term implantation can be performed. Furthermore, it is necessary to provide a drug delivery device that can store a drug such that there is no need to provide an additional storage and that can adjust a drug delivery rate.

<Prior Patent Literature> Korean Patent No. 10-2012-0032521

SUMMARY OF INVENTION

Technical Problem

Objects of the present invention to solve such problems described above are to provide a drug delivery device that is fixable to a biological tissue while minimizing damage thereto, can come into close contact with the biological tissue to directly deliver a drug thereto, and is economical as an additional drug storage is not needed and a method for manufacturing the drug delivery device.

Technical objects to be achieved by the present invention are not limited to the technical objects mentioned above, and the following description enables other unmentioned technical objects to be clearly understood by a person of ordinary skill in the art to which the present invention belongs.

Solution to Problem

According to a configuration of the present invention to achieve the object described above, there is provided a drug delivery device including a substrate unit that is inserted into a human body and has a porous insertion portion having one or more discharge voids. The insertion portion is provided to be deformable to match a shape of a biological tissue while expanding and contracting as a drug is injected into and discharged from an inside of the injection portion. The insertion portion is provided to deliver the injected drug to the biological tissue in a state of being in close contact with the biological tissue.

In an embodiment of the present invention, the drug delivery device may further include a measurement unit that is provided at one or both of one and the other surfaces of the substrate unit.

In the embodiment of the present invention, the drug delivery device may further include a circuit unit that is coupled to the substrate unit and has an IC chip connected to the measurement unit.

In the embodiment of the present invention, the substrate unit may further have a chip installed portion that is provided to be extended from the insertion portion and is coupled to the circuit unit.

In the embodiment of the present invention, the measurement unit may have one or more cables provided to be extended from the IC chip to the insertion portion, and one or more measurement portions that are positioned on the insertion portion and are provided separately from each other at each of the cables.

In the embodiment of the present invention, the measurement portion may be configured of one or more of sensors and electrodes and may be provided to be able to measure an electrical signal of the biological tissue and electrically stimulate the biological tissue.

In the embodiment of the present invention, the discharge voids may be provided to be positioned below the measurement portion.

In the embodiment of the present invention, the discharge voids may be provided to allow drugs of the same type and concentration to be injected into the discharge voids, or drugs, of which one or both of type and concentration are different from each other, to be injected into the discharge voids positioned on the different cables.

According to another configuration of the present invention to achieve the object described above, there is provided a method for manufacturing a drug delivery device, including: a) a step of preparing a lower substrate and an upper substrate; b) a step of forming a first masking pattern over the prepared upper substrate; c) a step of plasma treatment with the first masking pattern; d) a step of removing the first masking pattern; and e) a step of removing a carrier substrate under the lower substrate and injecting a drug.

In an embodiment of the present invention, the lower substrate may be provided to be prepared by forming a first polydimethylsiloxane (PDMS) spin-coating layer over the carrier substrate and forming a first Parylene layer by applying Parylene over the first PDMS spin-coating layer. The upper substrate may be provided to be prepared by forming a second PDMS spin-coating layer over the first Parylene layer.

According to still another configuration of the present invention to achieve the object described above, there is provided a method for manufacturing a drug delivery device, including: a) a step of preparing a lower substrate and an upper substrate; b) a step of performing selective adhesion between the prepared upper substrate and lower substrate; c) a step of forming a metal electrode layer over the adhesion-performed upper substrate; d) a step of forming an insulation layer on the metal electrode layer; and e) a step of removing a carrier substrate under the lower substrate and injecting a drug.

In an embodiment of the present invention, the lower substrate may be provided to be prepared by forming a first polydimethylsiloxane (PDMS) spin-coating layer over the carrier substrate and forming a first Parylene layer by applying Parylene over the first PDMS spin-coating layer. The upper substrate may be provided to be prepared by forming a second PDMS spin-coating layer over the first Parylene layer.

In the embodiment of the present invention, the step of b) may include: b1) a step of forming first masking patterns over the prepared upper substrate; b2) a step of irradiating plasma to the substrate with the first masking patterns; and b3) a step of removing the first masking patterns.

In the embodiment of the present invention, in the step of b1), a plurality of the first masking patterns may be provided separately from each other. In the step of b2), the plasma with which irradiation is performed toward the upper substrate with the first masking patterns may cause the first Parylene layer positioned at an outer side of the first masking patterns to adhere to the upper substrate.

In the embodiment of the present invention, the step of c) may include: c1) a step of forming a second Parylene layer by applying Parylene over the upper substrate; c2) a step of forming a metal thin-film layer by applying a metal thin-film over the second Parylene layer; c3) a step of forming second masking patterns over the applied metal thin-film layer; c4) a step of forming the metal electrode layer by patterning the metal thin-film layer by using the second masking patterns; and c5) a step of removing the second masking patterns.

In the embodiment of the present invention, in the step of c3), a plurality of the second masking patterns may be provided separately from each other to be positioned above the first Parylene layer which does not adhere to the upper substrate.

In the embodiment of the present invention, the step of d) may include: d1) a step of forming a third Parylene layer by applying Parylene on the metal electrode layer; d2) a step of forming third masking patterns over the third Parylene layer; d3) a step of forming the insulation layer by irradiating plasma to the third Parylene layer with the third masking patterns and etching the third Parylene layer according to pattern shapes of the third masking patterns; and d4) a step of removing the third masking patterns.

In the embodiment of the present invention, in the step of d2), the third masking patterns may be formed over the third Parylene layer and formed at positions corresponding to both end portions of the metal electrode layer.

Advantageous Effects of Invention

According to configurations described above, effects of the present invention are as follows. A measurement unit can come into close contact with a biological tissue to stably measure an electrical signal of the biological tissue at a predetermined position and apply electrical stimulation to the biological tissue.

In addition, according to the present invention, a drug can be accurately injected only into a part of the biological tissue.

In addition, according to the present invention, an insertion portion of a substrate unit is inserted into a biological tissue in a contracted state, and thus an incision area can be minimized. As described above, when the incision area of the biological tissue is small, it is possible to prevent the occurrence of problems of bacterial penetration and infection into an incision site during or after a medical procedure, and a patient can quickly recover after the medical procedure.

Besides, the insertion portion can be provided to expand in a state of being completely inserted into the biological tissue, thus coming into close contact with the biological tissue without an additional instrument. Consequently, when patients move their head, or even when the patients do activity, there is no risk of detachment of the insertion portion from the biological tissue, and thus the present invention can be stably used.

In addition, a substrate unit is made of an elastomer material and expands into a flexible balloon shape, and thus shape compensation can be easily made depending on movement of the biological tissue. Consequently, even when the substrate unit according to the present invention is stably inserted into the biological tissue for a long time, it is possible for the biological tissue not to be damaged.

In addition, according to the present invention, a circuit unit is conveniently provided to be integrally attached to the substrate unit so as to measure an electrical signal of the biological tissue and apply electrical simulation to the biological tissue without an additional device.

The effects of the present invention are construed not to be limited to the above-mentioned effects but to include every effect that can be derived from the configurations of the invention described in the detailed description of the embodiments or claims of the present invention.

DESCRIPTION OF PREFERRED EMBODIMENT

A preferred embodiment of the present invention includes: a substrate unit that is inserted into a human body and has a porous insertion portion having one or more discharge voids. The insertion portion is provided to be deformable to match a shape of a biological tissue while expanding and contracting as a drug is injected into and discharged from an inside of the injection portion. The insertion portion is provided to deliver the injected drug to the biological tissue in a state of being in close contact with the biological tissue.

DESCRIPTION OF EMBODIMENTS

Hereinafter, the present invention will be described with reference to the accompanying drawings. However, the present invention can be realized as various different examples, thus not being limited to embodiments described here. Besides, parts irrelevant to the description are omitted from the drawings in order to clearly describe the present invention, and similar reference signs are assigned to similar parts through the entire specification.

In the entire specification, a case where a certain part "is connected to (accesses, is in contact with, or is coupled to)" another part includes not only a case where the parts are "directly connected" to each other, but also a case where the parts are "indirectly connected" to each other with another member interposed therebetween. In addition, a case where a certain part "includes" a certain configurational element means a case where another configurational element is not excluded but can be further included, unless specifically described otherwise.

Terms used in this specification are only used to describe a specific embodiment and are not intentionally used to limit the present invention thereto. A word having a singular form contain a meaning of its plural forms, unless obviously implied otherwise in context. In this specification, words such as "to include" or "to have" are construed to specify that a feature, a number, a step, an operation, a configurational element, a member, or a combination thereof described in the specification is present and not to exclude presence or a possibility of addition of one or more other features, numbers, steps, operations, configurational elements, members, or combinations thereof in advance.

Hereinafter, embodiments of the present invention will be described in detail with reference to the accompanying drawings.

Figure 1A:
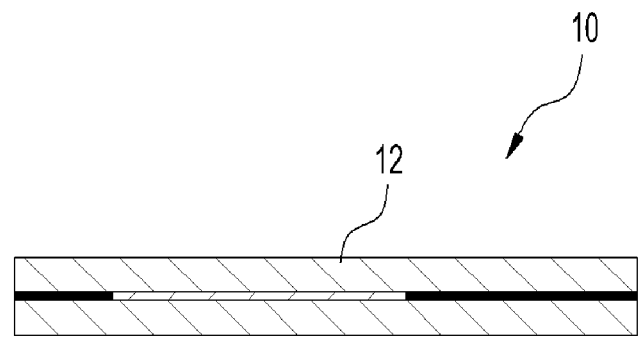
FIGS. 1A and 1B are views illustrating a drug delivery device according to a first embodiment of the present invention.
Figure 1B:
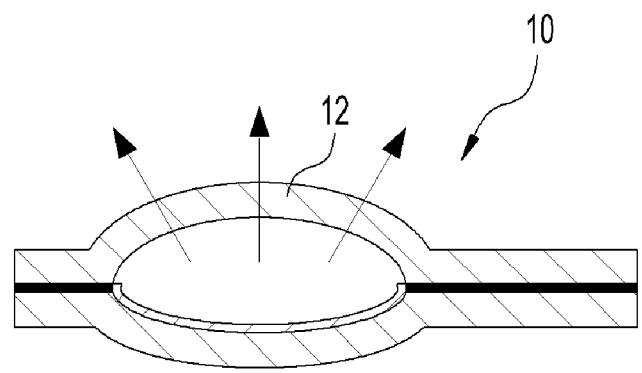
Figure 2:
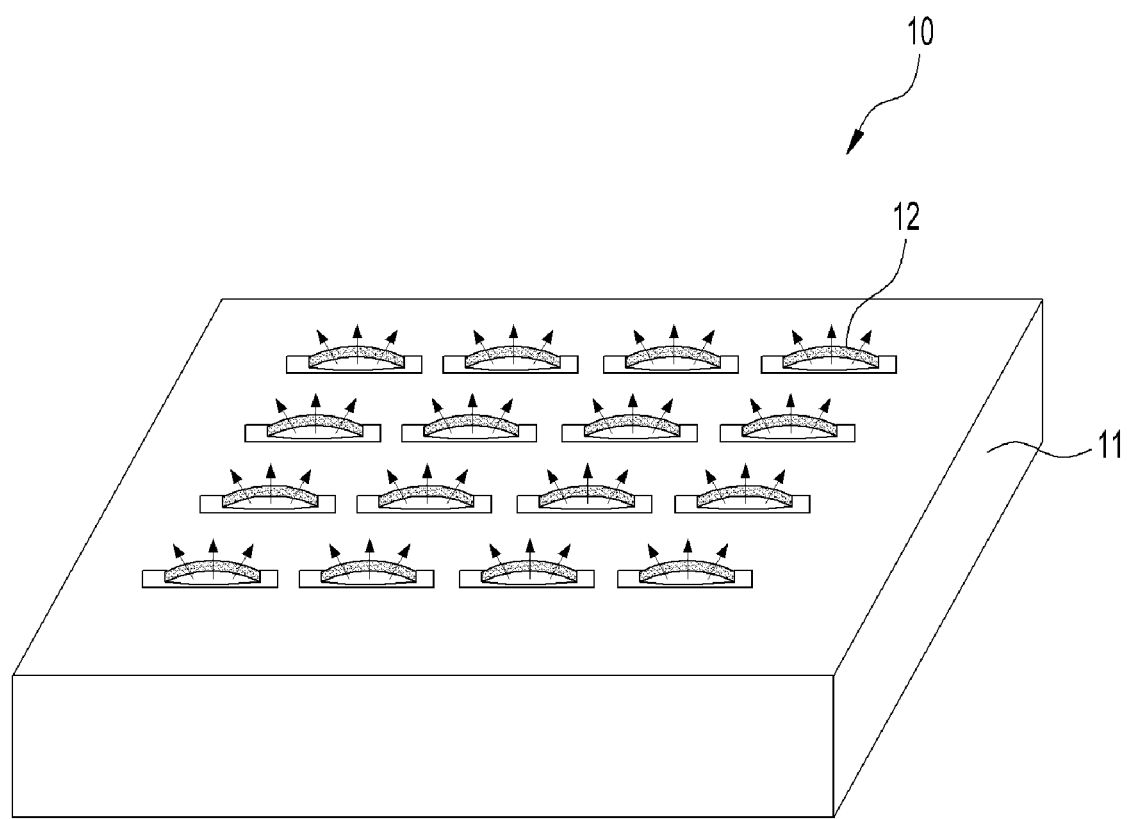
FIG. 2 is a perspective view of the drug delivery device according to the first embodiment of the present invention.

FIG. 1 is a view illustrating a drug delivery device according to a first embodiment of the present invention, and FIG. 2 is a perspective view of the drug delivery device according to the first embodiment of the present invention.

As illustrated in FIGS. 1 and 2, a drug delivery device 10 according to the first embodiment includes a substrate unit 11.

The substrate unit 11 of the drug delivery device 10 is provided to be inserted into a human body, and the substrate unit 11 can have one or more discharge voids 12.

Besides, as illustrated in (a) and (b) of FIG. 1, the substrate unit 11 is provided to be deformable to match a shape of a biological tissue while expanding and contracting as a drug is injected into and discharged from an inside of the substrate unit, and the discharge voids 12 of the substrate unit 11 can be provided to deliver the injected drug to the biological tissue in a state where the substrate unit 11 is in close contact with the biological tissue.

As illustrated in FIG. 2, the discharge voids 12 can be provided to be arranged in a plurality of rows and columns on the substrate unit 11; however, arrangement of the discharge voids is not limited thereto. Besides, the discharge voids 12 provided as described above enables a different drug to be injected for each row or column thereof, and the discharge voids 12 can have different porosity from each other.

As an example, when a void size of the discharge voids positioned along an A row is 1 μm, and the void size of the discharge voids positioned along a B row is 2 μm, an injection rate of a drug into the discharge voids positioned on the B row is twice an injection rate of a drug into the discharge voids positioned on the A row.

As described above, when the void size of the discharge voids is different for each row, the injection rate of the drug can be variously controlled for each position, and a concentration of the drug can be easily controlled.

The void size of the discharge void can be easily adjusted by putting and melting polyethylene glycol (PEG) at positions of the substrate unit 11 made of PDMS at which the discharge voids 12 are formed, performing the etching using oxygen plasma, and initiating a crack in a surface of the substrate unit 11.

The substrate unit 11 of the drug delivery device 10 provided as described above is made of an elastomer to expand and fix to match the shape of the biological tissue. Hence, the substrate unit does not damage the biological tissue during fixing and can be inserted into a human body for a long time.

In addition, according to the present invention, the substrate unit 11 is provided to store a drug, and thus there is no need to provide a separate drug storage.

In addition, it is possible to easily adjust the injection rate of various drugs by adjusting the porosity of the discharge voids 12.

Figure 3:
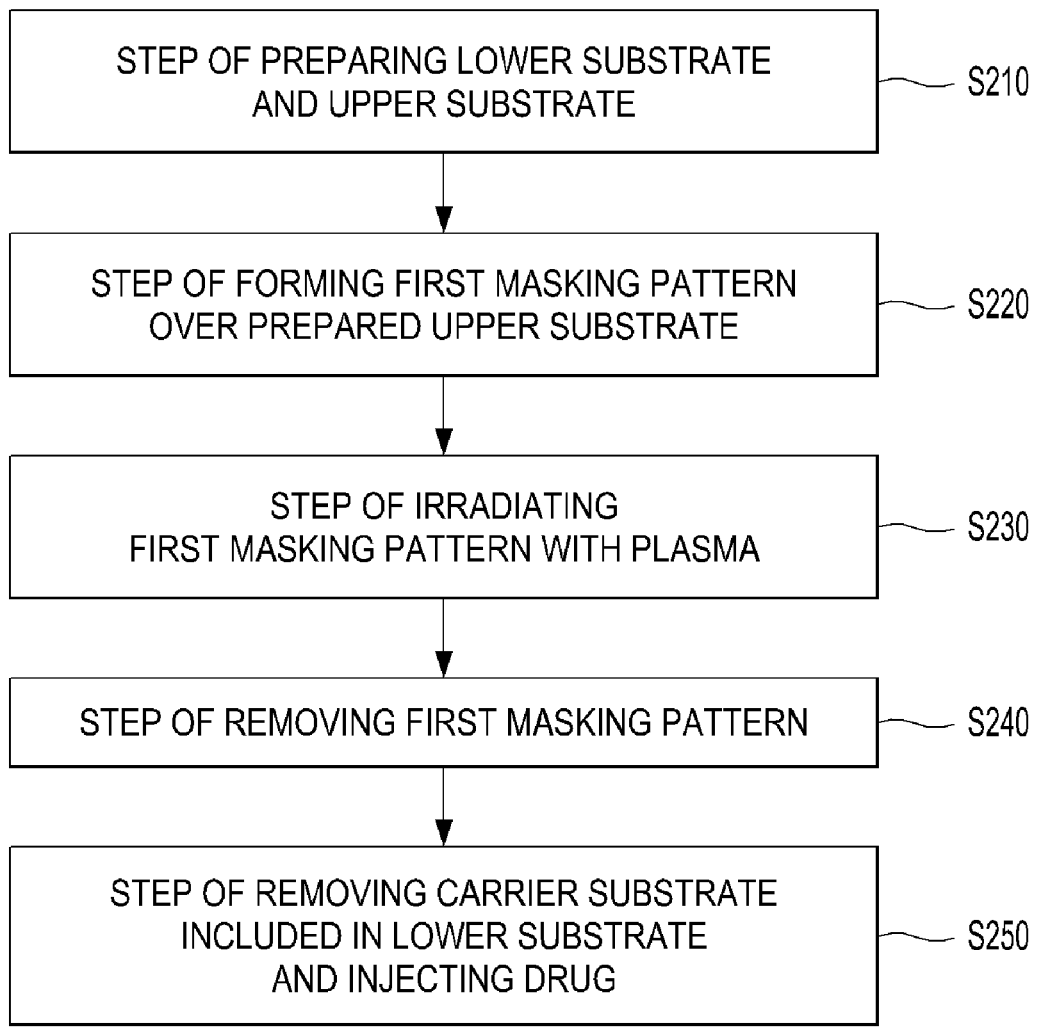
FIG. 3 is a flowchart of a method for manufacturing the drug delivery device according to the first embodiment of the present invention.
Figure 4:
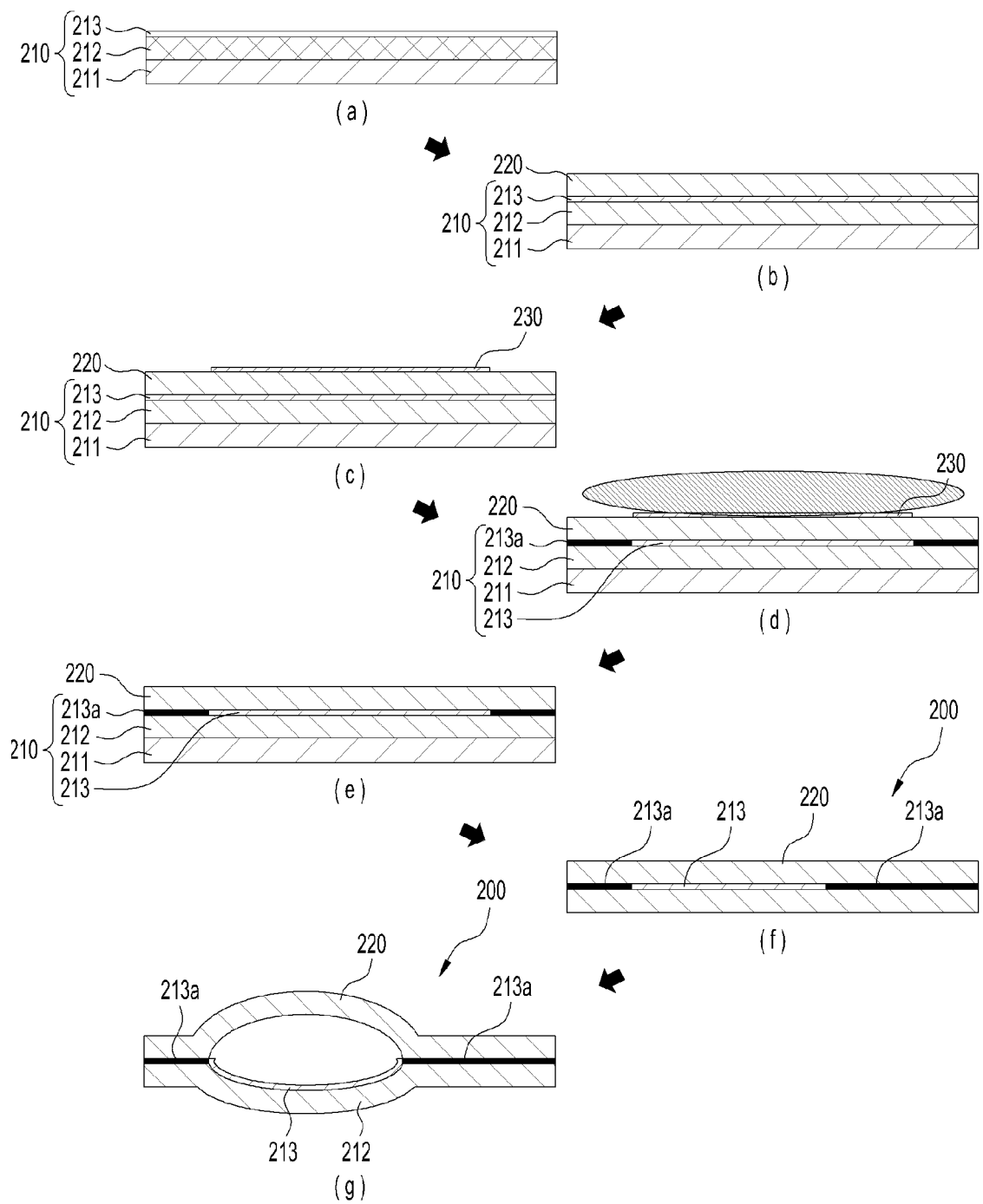
FIG. 4 is a view illustrating processes of the method for manufacturing the drug delivery device according to the first embodiment of the present invention.

FIG. 3 is a flowchart of a method for manufacturing the drug delivery device according to the first embodiment of the present invention, and FIG. 4 is a view illustrating processes of the adhering method for manufacturing the drug delivery device according to the first embodiment of the present invention.

As illustrated in FIGS. 3 and 4, in the method for manufacturing a drug delivery device 200 according to the first embodiment, first, Step S210 of preparing a lower substrate and an upper substrate can be performed.

In Step S210 of preparing the lower substrate and the upper substrate, as illustrated in (a) of FIG. 4, first, the lower substrate 210 can be provided to be prepared by forming a first polydimethylsiloxane (PDMS) spin-coating layer 212 over a carrier substrate 211 and forming a first Parylene layer 213 by applying Parylene over the first PDMS spin-coating layer 212 so as to be coupled thereto.

As illustrated in (b) of FIG. 4, the upper substrate 220 can be provided to be prepared by forming a second PDMS spin-coating layer 220 over the first Parylene layer 213.

Here, the lower substrate 210 and the upper substrate 220 can be prepared simultaneously, or the upper substrate 220 can be prepared before the lower substrate 210.

In addition, the lower substrate 210 and the upper substrate 220 correspond to a substrate unit 110 of a drug delivery device 100.

After Step S210 of preparing the lower substrate and the upper substrate, Step S220 of forming first masking patterns over the prepared upper substrate is performed.

In Step S220 of forming the first masking patterns over the prepared upper substrate, the first masking patterns 230 can be formed to have pattern shapes at parts at which the upper substrate 220 and the lower substrate 210 are not joined to each other, as illustrated in (c) of FIG. 4.

In other words, when the upper substrate 220 and the lower substrate 210 adhere to each other, the adhering positions can be determined depending on the pattern shapes of the first masking patterns 230.

After Step S220 of forming the first masking patterns over the prepared upper substrate, Step S230 of irradiating plasma to the substrate with the first masking patterns can be performed.

In Step S230 of irradiating plasma to the substrate with the first masking patterns, the plasma with which irradiation is performed toward the upper substrate with the first masking patterns 230 enables the first Parylene layer 213 positioned at an outer side of the first masking patterns 230 to adhere to the upper substrate 220, as illustrated in (d) of FIG. 4.

In other words, the plasma with which the irradiation is performed toward the upper substrate with the first Parylene layer 213 can heat parts which are not blocked by the first masking patterns 230 such that the upper substrate 220 and the lower substrate 210 adhere to each other.

In addition, the plasma can be $N_2/O_2$ plasma; however, the plasma is not limited thereto.

In addition, in Step S230 of irradiating plasma to the substrate with the first masking patterns, the discharge voids can be formed by putting and melting polyethylene glycol (PEG) at positions of the upper substrate 220 made of PDMS at which the discharge voids are formed, performing the etching using the plasma, and initiating a crack in a surface of the upper substrate 220.

After Step S230 of irradiating plasma to the substrate with the first masking patterns, Step S240 of removing the first masking patterns can be performed, as illustrated in (e) of FIG. 4.

After Step S240 of removing the first masking patterns, Step S250 of removing the carrier substrate under the lower substrate and injecting a drug can be performed.

In Step S250 of removing the carrier substrate under the lower substrate and injecting a drug, first, the carrier substrate 211 can be removed, as illustrated in (f) of FIG. 4.

Subsequently, as illustrated in (g) of FIG. 4, a drug can be injected into a channel formed between the upper substrate 220 and the lower substrate 210 such that the injected drug can be delivered to a biological tissue.

Figure 5:
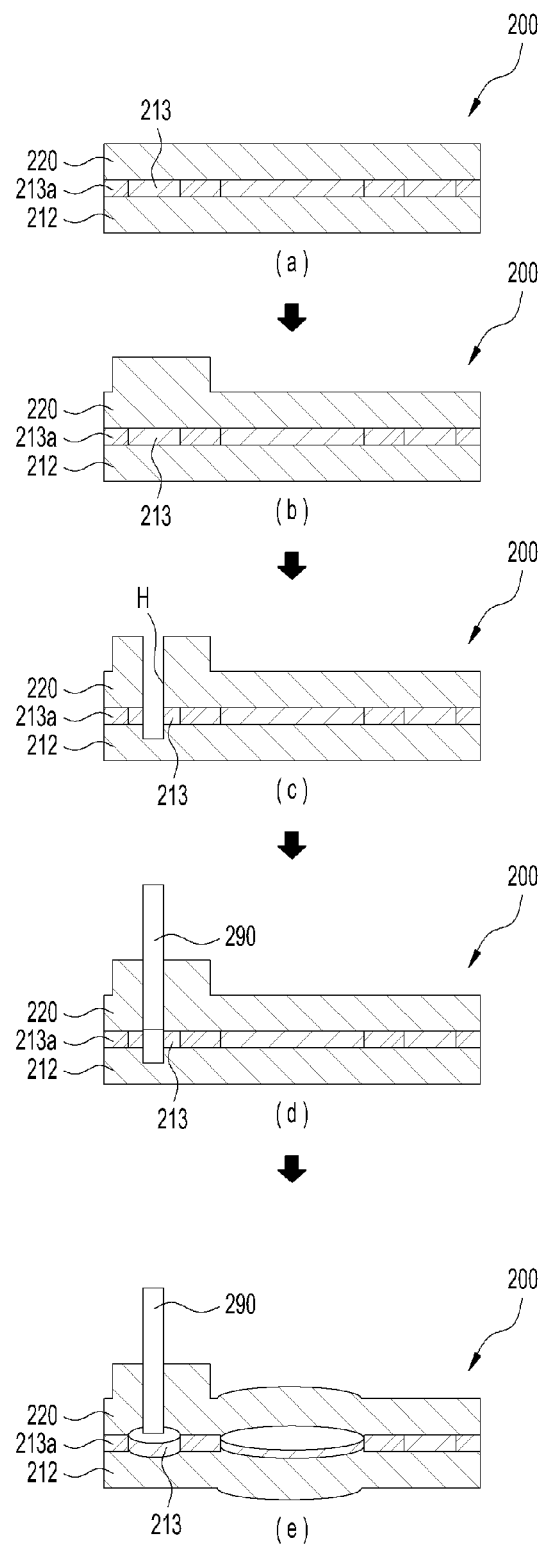
FIG. 5 is a view illustrating processes of a method for injecting a drug to the drug delivery device according to the first embodiment of the present invention.

FIG. 5 is a view illustrating processes of a method for injecting a drug to the drug delivery device according to the first embodiment of the present invention.

With reference to FIG. 5, the method for injecting a drug into the drug delivery device 200 according to the first embodiment provided as described above is described.

First, the drug delivery device 200 in which the lower substrate 210 and the upper substrate 220 are selectively bonded to each other as described above is prepared. Besides, a through-hole H can be formed at a part of the first Parylene layer 213 at which an adhesive layer 213a is not formed.

The through-hole H can be formed to penetrate the first PDMS spin-coating layer 212 from the upper substrate 220 by a predetermined depth.

Besides, an injection port 290 is inserted into the through-hole H, and the lower substrate 210 and the upper substrate 220 can be caused to expand and contract by injecting or discharging a drug through the injection port 290.

In other words, in accordance with the method provided as described above, an insertion portion 111 of the drug delivery device 100 can expand and contract, and the injected drug can be delivered through the upper substrate 220 to the biological tissue.

Figure 6:
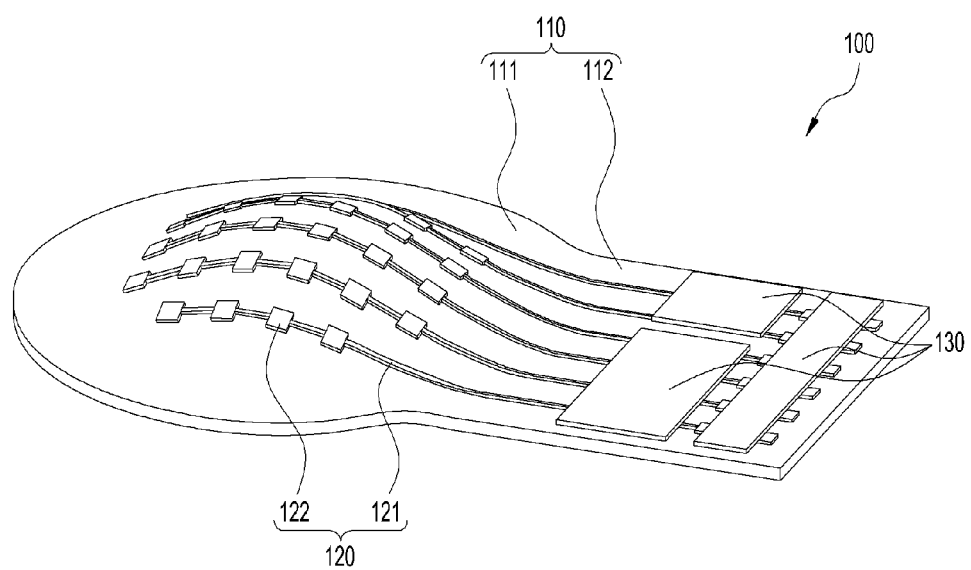
FIG. 6 is a perspective view of a drug delivery device including an electrode according to second and third embodiments of the present invention.

FIG. 6 is a perspective view of a drug delivery device including an electrode according to second and third embodiments of the present invention.

As illustrated in FIG. 6, the drug delivery device 100 includes the substrate unit 110, a measurement unit 120, and a circuit unit 130.

The substrate unit 110 includes an insertion portion 111 and a chip installed portion 112.

The insertion portion 111 is provided to be inserted into the biological tissue and can be provided to expand and contract.

Specifically, the insertion portion 111 can be provided to expand and contract as a drug is injected into and discharged from an inside thereof, and the insertion portion 111 can be deformed to match a shape of the biological tissue to come into close contact with the biological tissue when the insertion portion 111 expand. Consequently, according to the present invention, even when a patient moves, there is no risk of detachment of the insertion portion 111 from the biological tissue, and thus the insertion portion is stably attached to the biological tissue.

The insertion portion 111 can be made of an elastomer material. Consequently, the insertion portion 111 expands into a flexible balloon shape, and thus shape compensation can be easily made following movement of a connected cable. Consequently, even when the substrate unit 110 according to the present invention is inserted into the biological tissue for a long time, it is possible not to damage the biological tissue. However, a material of the insertion portion 111 is not limited to an elastomer and includes any material that can have an effect similar to that of the elastomer.

The insertion portion 111 provided as described above can come into a contracted state when being inserted into the biological tissue, and the insertion portion 111 can expand when the insertion portion is completely inserted into a preset position.

At this point, the biological tissue can be in a state of being incised by a size which only allows the insertion portion 111 to pass.

In other words, according to the present invention, the insertion portion 111 of the substrate unit 110 is inserted into the biological tissue in a contracted state, and thus an incision area of the biological tissue can be minimized. As described above, when the incision area of the biological tissue is small, it is possible to prevent problems of bacterial penetration and infection into an incision site during or after a medical procedure, and a patient can quickly recover after the medical procedure.

In addition, similarly to the balloon, the insertion portion 111 can expand and contract depending on injection and discharge of the drug, thus is economical in that the insertion portion can be fixed to a biological tissue regardless of a size or shape of a biological tissue different for each person.

The chip installed portion 112 can be provided to be extended from the insertion portion 111 and can have a configuration in which the circuit unit 130 is coupled thereto.

Specifically, when the insertion portion 111 is inserted into the biological tissue, the chip installed portion 112 can be provided to be positioned outside the biological tissue, and one or more of the circuit units 130 can be installed at the chip installed portion 112.

The measurement unit 120 can be provided at one or both of one surface and the other surface of the substrate unit 110 and has cables 121 and measurement portions 122.

The cable 121 can be provided to be extended from an IC chip of the circuit unit 130 to the insertion portion 111.

One or more of the measurement portions 122 can be provided on each of the cables 121 positioned on the insertion portion 111 and can be provided in a length direction of the cables 121. Besides, the measurement portions 122 can be configured of one or more of sensors and electrodes and can be provided to measure an electrical signal of the biological tissue and electrically stimulate the biological tissue.

When the insertion portion 111 expands, the measurement portions 122 provided as described above can come into close contact with the biological tissue to stably measure the electrical signal of the biological tissue at a predetermined position and apply electrical stimulation to the biological tissue.

In addition, the insertion portion 111 of the substrate unit 110 according to the present invention can be provided to deliver the injected drug to the biological tissue in a state of being in close contact with the biological tissue.

Specifically, the insertion portion 111 of the present invention has the discharge voids to be porous. Besides, the drug injected into the substrate unit 110 can be delivered to the biological tissue, through the discharge voids formed as described above.

The discharge voids can be provided to be arranged in a plurality of rows and columns on the insertion portion 111; however, arrangement of the discharge voids is not limited thereto. Besides, the discharge voids provided as described above enables a different drug to be injected for each row thereof.

According to the first embodiment, as illustrated in the drawings, the discharge voids can be provided at positions corresponding to the measurement portions 122. In other words, the discharge voids can be provided in the length direction of the cables 121, and drugs of the same type and concentration can be injected into the discharge voids, or drugs, of which one or both of type and concentration are different from each other, can be injected into the discharge voids positioned on the different cables 121.

Besides, the discharge voids positioned on the same cables 121 can have the same void size, and the discharge voids positioned on different cables 121 can have a void size different from each other.

As an example, when the void size of the discharge voids positioned along an A cable is 1 μm, and the void size of the discharge voids positioned along a B cable is 2 μm, an injection rate of a drug into the discharge voids positioned on the B cable is twice an injection rate of a drug into the discharge voids positioned on the A cable.

As described above, when the void size of the discharge voids is different for each of the cables 121, the injection rate of the drug can be variously controlled for each position, and a concentration of the drug can be easily controlled.

The void size of the discharge void can be easily adjusted by putting and melting polyethylene glycol (PEG) at positions of the insertion portion 111 made of PDMS at which the discharge voids are formed, performing the etching using oxygen plasma, and initiating a crack in a surface of the insertion portion 111.

On the other hand, it is possible for the measurement unit 120 not to be provided in a case of needing only the drug delivery to the biological tissue, and more measurement units can be provided in a case of needing electrical stimulation and recording from the biological tissue.

The circuit unit 130 can be provided to be coupled to the substrate unit 110 and have IC chips connected to the measurement unit 120. The drug delivery device 100 provided as described above is conveniently used by having the circuit unit 130 that is provided to be integrally attached to the substrate unit 110 so as to measure the electrical signal of the biological tissue and apply the electrical simulation to the biological tissue without an additional device.

In addition, the circuit unit 130 can be provided to be capable of performing wireless communication so as to perform post-processing of the electrical signal.

Figure 7:
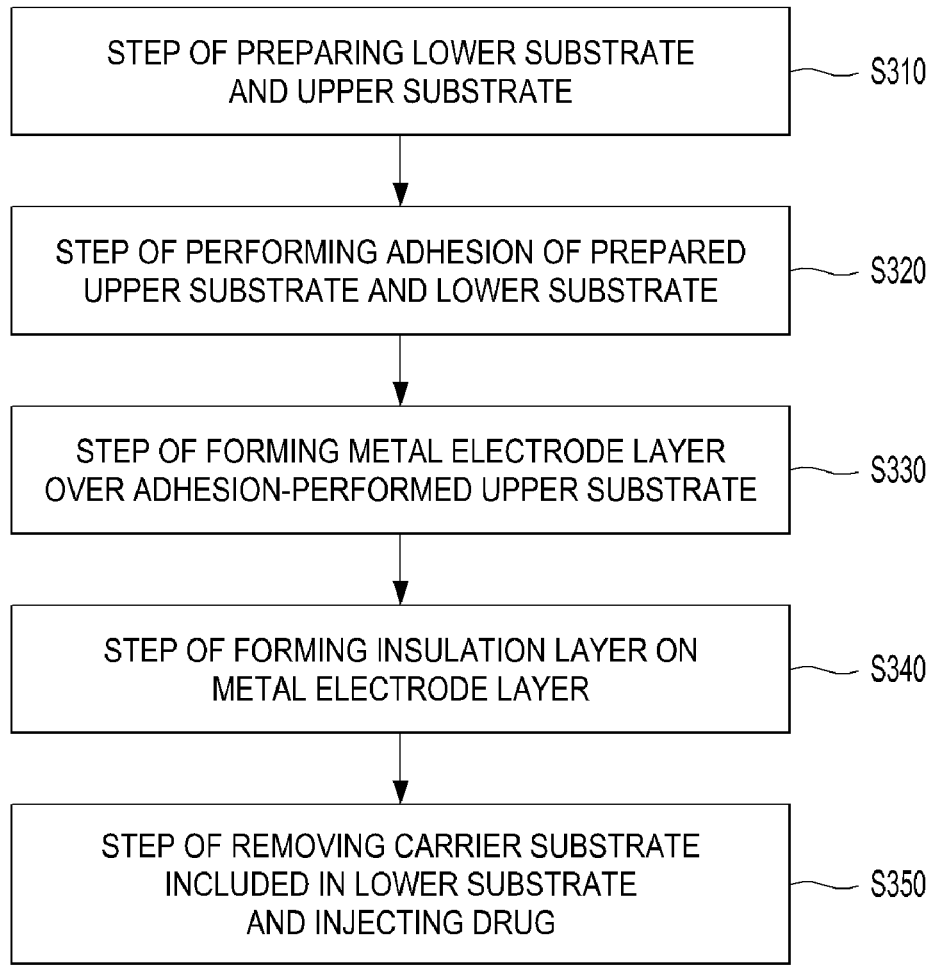
FIG. 7 is a flowchart of a method for manufacturing the drug delivery device according to the second embodiment of the present invention.
Figure 8:
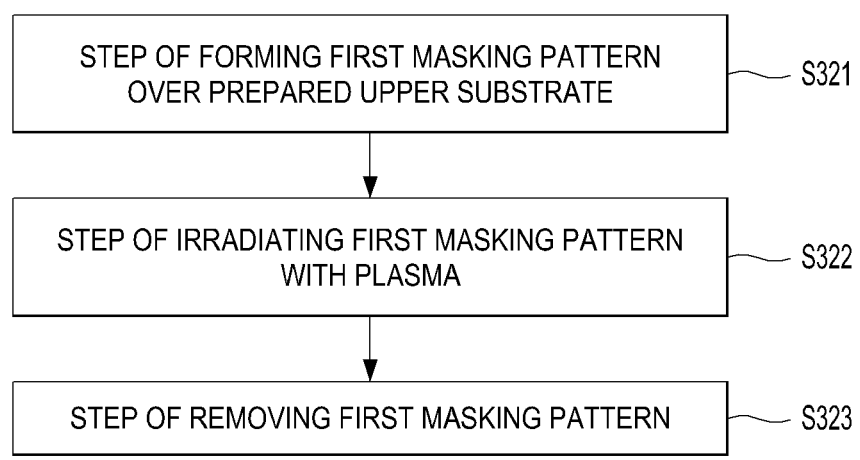
FIG. 8 is a flowchart of a step of performing adhesion according to the second embodiment of the present invention.
Figure 9:
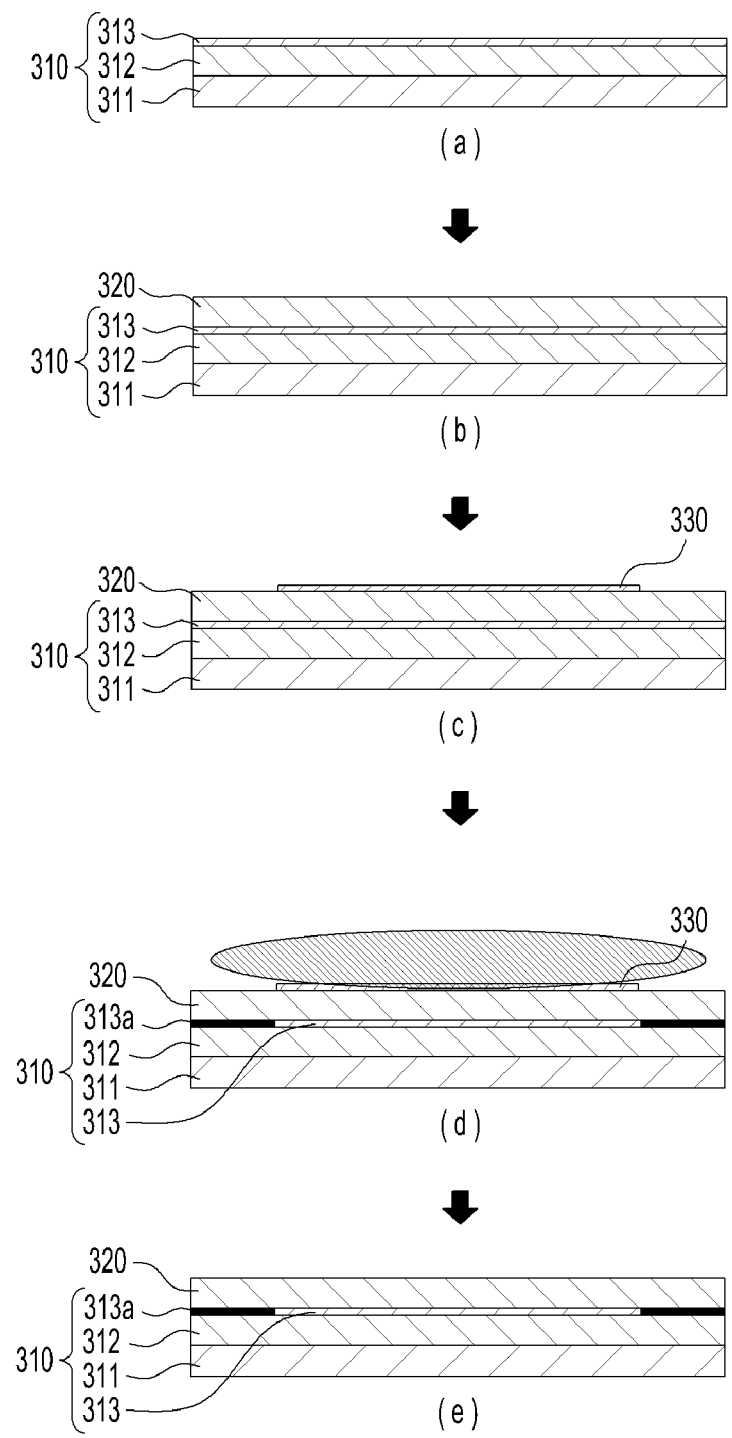
FIG. 9 is a view illustrating processes of a step of performing preparation and the step of performing the adhesion according to the second embodiment of the present invention.

FIG. 7 is a flowchart of a method for manufacturing the drug delivery device according to the second embodiment of the present invention, FIG. 8 is a flowchart of a step of performing adhesion according to the second embodiment of the present invention, and FIG. 9 is a view illustrating processes of a step of performing preparation and the step of performing the adhesion according to the second embodiment of the present invention.

As illustrated in FIGS. 7 to 9, in the method for manufacturing a drug delivery device 300 according to the second embodiment, first, Step S310 of preparing a lower substrate and an upper substrate can be performed.

In Step S310 of preparing the lower substrate and the upper substrate, as illustrated in (a) of FIG. 9, first, the lower substrate 310 can be provided to be prepared by forming a first polydimethylsiloxane (PDMS) spin-coating layer 312 over a carrier substrate 311 and forming a first Parylene layer 313 by applying Parylene over the first PDMS spin-coating layer 312 so as to be coupled thereto.

As illustrated in (b) of FIG. 9, the upper substrate 320 can be provided to be prepared by forming a second PDMS spin-coating layer 320 over the first Parylene layer 313.

Here, the lower substrate 310 and the upper substrate 320 can be prepared simultaneously, or the upper substrate 320 can be prepared before the lower substrate 310.

In addition, the lower substrate 310 and the upper substrate 320 correspond to the substrate unit 110 of the drug delivery device 100.

After Step S310 of preparing the lower substrate and the upper substrate, Step S320 of performing selective adhesion between the prepared upper substrate and lower substrate can be performed.

After Step S320 of performing the selective adhesion between the prepared upper substrate and lower substrate, first, Step S321 of forming first masking patterns over the prepared upper substrate is performed.

In Step S321 of forming the first masking patterns over the prepared upper substrate, the first masking patterns 330 can be formed to have pattern shapes at parts at which the upper substrate 320 and the lower substrate 310 are not joined to each other, as illustrated in (c) of FIG. 9.

In other words, when the upper substrate 320 and the lower substrate 310 adhere to each other, the adhering positions can be determined depending on the pattern shapes of the first masking patterns 330.

After Step S321 of forming the first masking patterns over the prepared upper substrate, Step S322 of irradiating plasma to the substrate with the first masking patterns can be performed.

In Step S322 of irradiating plasma to the substrate with the first masking patterns, the plasma with which irradiation is performed toward the upper substrate with the first masking patterns 330 enables the first Parylene layer 313 positioned at an outer side of the first masking patterns 330 to adhere to the upper substrate 320, as illustrated in (d) of FIG. 9.

In other words, the plasma with which the irradiation is performed toward the upper substrate with the first Parylene layer 313 can heat parts which are not blocked by the first masking patterns 330 such that the upper substrate 320 and the lower substrate 310 adhere to each other.

In addition, the plasma can be $N_2/O_2$ plasma; however, the plasma is not limited thereto.

In addition, in Step S322 of irradiating plasma to the substrate with the first masking patterns, discharge voids can be formed by putting and melting polyethylene glycol (PEG) at positions of the upper substrate 320 made of PDMS at which the discharge voids are formed, performing the etching using the plasma, and initiating a crack in a surface of the upper substrate 320.

After Step S322 of irradiating plasma to the substrate with the first masking patterns, Step S323 of removing the first masking patterns can be performed, as illustrated in (e) of FIG. 9.

Figure 10:
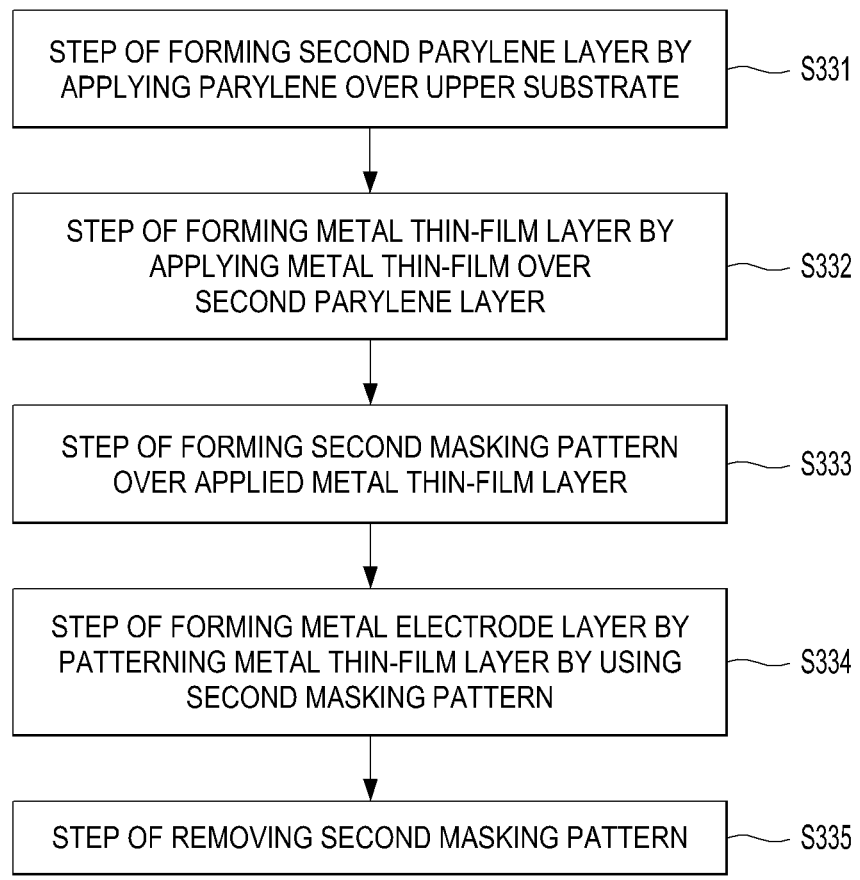
FIG. 10 is a flowchart of a step of forming a metal electrode layer according to the second embodiment of the present invention.
Figure 11:
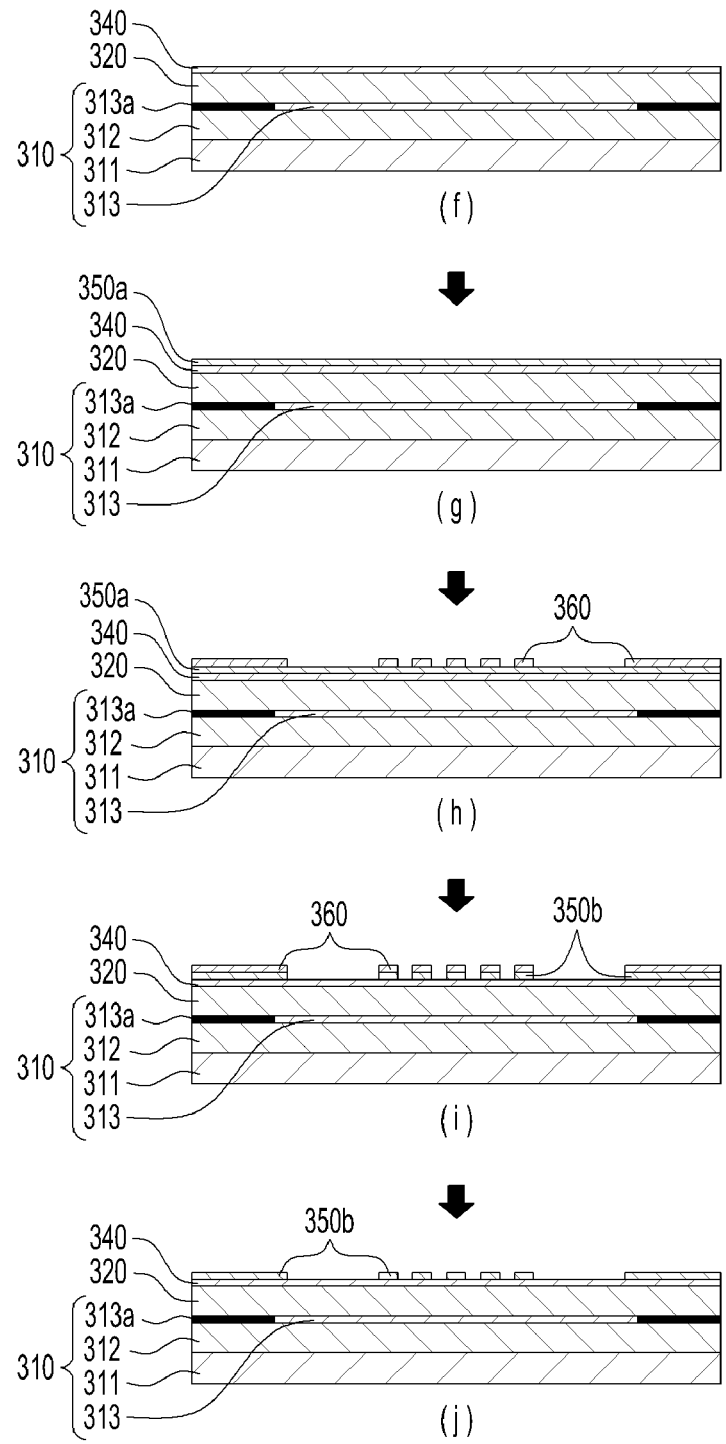
FIG. 11 is a view illustrating processes of the step of forming the metal electrode layer according to the second embodiment of the present invention.

FIG. 10 is a flowchart of a step of forming a metal electrode layer according to the second embodiment of the present invention, and FIG. 11 is a view illustrating processes of the step of forming the metal electrode layer according to the second embodiment of the present invention.

As illustrated in FIGS. 7, 10, and 11, after Step S320 of performing the selective adhesion between the prepared upper substrate and lower substrate, Step S330 of forming the metal electrode layer above the adhesion-performed upper substrate can be performed.

Besides, in Step S330 of forming the metal electrode layer above the adhesion-performed upper substrate, first, Step S331 of forming a second Parylene layer by applying Parylene over the upper substrate can be performed.

In Step S331 of forming the second Parylene layer by applying Parylene over the upper substrate, a second Parylene layer 340 can be formed by applying Parylene over the upper substrate 310, the Parylene being provided for applying a metal electrode, as illustrated in (f) of FIG. 11.

After Step S331 of forming the second Parylene layer by applying Parylene over the upper substrate, Step S332 of forming a metal thin-film layer by applying a metal thin-film over the second Parylene layer can be performed.

In Step S332 of forming the metal thin-film layer by applying the metal thin-film over the second Parylene layer, the metal thin-film is applied over the second Parylene layer 340, and thereby a metal thin-film layer 350a can be formed, as illustrated in (g) of FIG. 11.

Here, the metal thin-film of the metal thin-film layer 350a can contain Cr, Ti, Au, Pt, or the like.

In addition, when the metal thin-film is applied to form the metal thin-film layer 350a, a sputter and an evaporator can be used.

After Step S332 of forming the metal thin-film layer by applying the metal thin-film over the second Parylene layer, Step S333 of forming second masking patterns over the applied metal thin-film can be performed.

In Step S333 of forming the second masking patterns over the applied metal thin-film, second masking patterns 360 can be formed over the metal thin-film layer 350a, as illustrated in (h) of FIG. 11.

The second masking patterns 360 can be provided to form a metal electrode layer 350b by patterning the metal thin-film layer 350a, and thus the second masking patterns 360 can be provided to have pattern shapes corresponding to a preset shape of the metal electrode layer 350b.

After Step S333 of forming the second masking patterns over the applied metal thin-film, Step S334 of forming the metal electrode layer by patterning the metal thin-film layer by using the second masking patterns can be performed.

In Step S334 of forming the metal electrode layer by patterning the metal thin-film layer by using the second masking patterns, the metal electrode layer 350b can be formed by patterning the metal thin-film layer 350a according to the second masking patterns 360. More specifically, as illustrated in (i) of FIG. 11, in Step S334 of forming the metal electrode layer by patterning the metal thin-film layer by using the second masking patterns, the metal electrode layer 350b can be formed by etching and patterning the metal thin-film layer 350a according to the pattern shapes of the second masking patterns 360 through a wet etching process.

The wet etching process is performed on the metal thin-film layer 350a in a state where the second masking patterns 360 are settled over the metal thin-film layer, and thus etching of the metal thin-film layer can be rapidly and accurately performed at low costs.

In addition, after the metal electrode layer 350b is formed, a metal insulation layer can be further formed on the metal electrode layer 350b.

After Step S334 of forming the metal electrode layer by patterning the metal thin-film layer by using the second masking patterns, Step S335 of removing the second masking patterns can be performed, as illustrated in (j) of FIG. 11.

The metal electrode layer 350b provided as described above corresponds to the measurement unit 120 of the drug delivery device 100.

Figure 12:
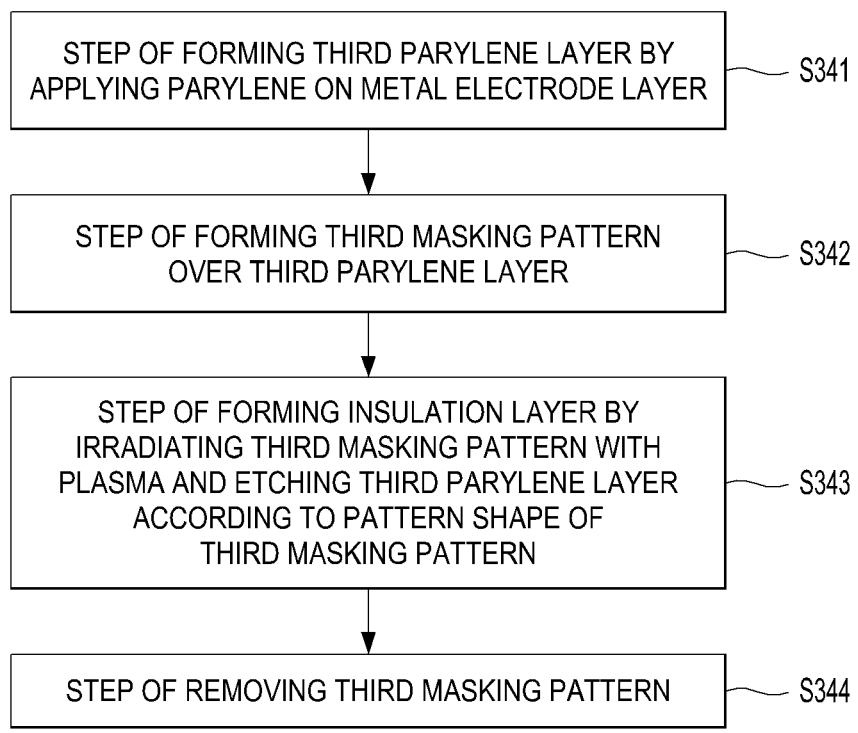
FIG. 12 is a flowchart of a step of forming an insulation layer according to the second embodiment of the present invention.
Figure 13:
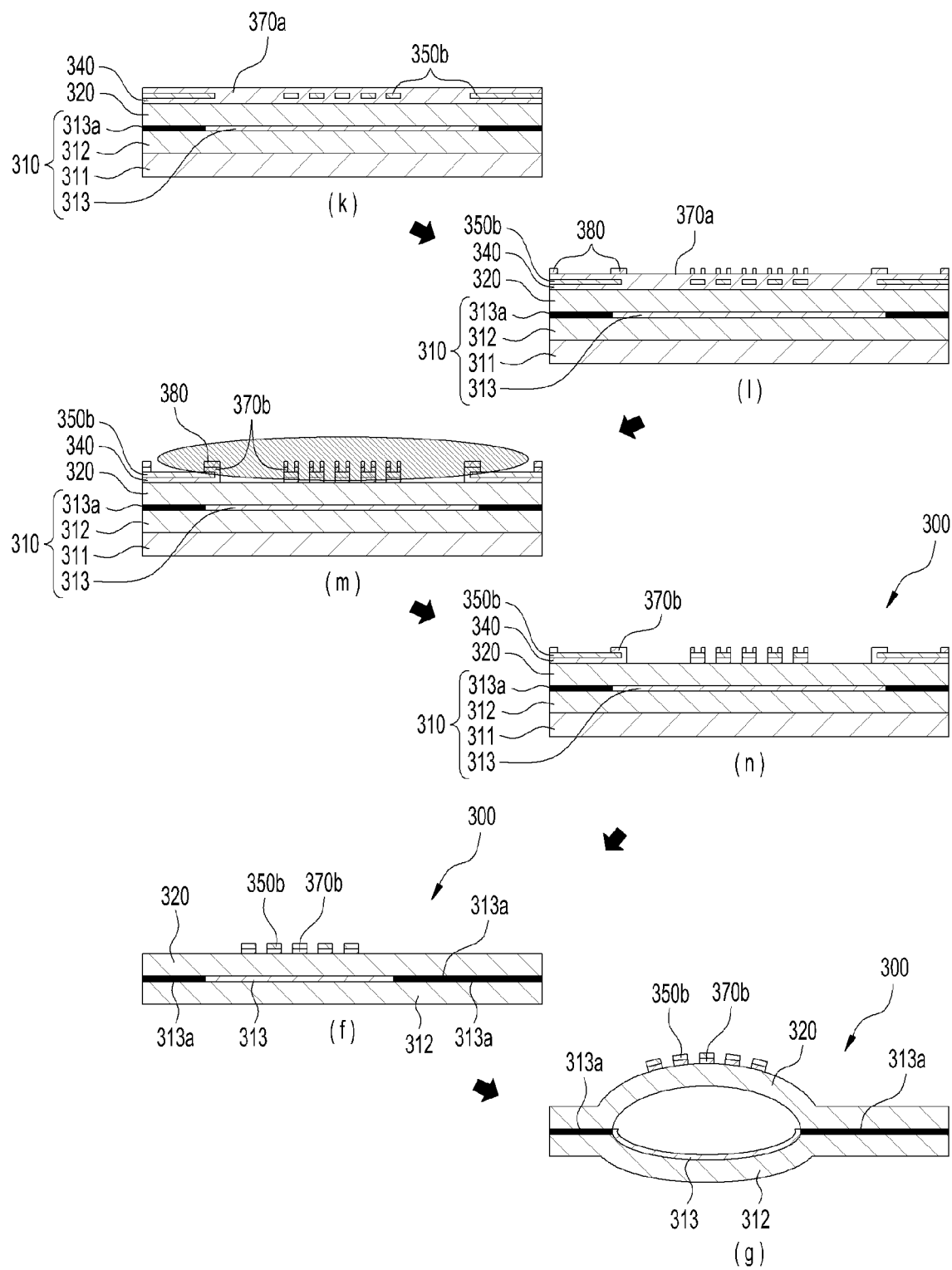
FIG. 13 is a view illustrating processes of the step of forming the insulation layer according to the second embodiment of the present invention.

FIG. 12 is a flowchart of a step of forming an insulation layer according to the second embodiment of the present invention, and FIG. 13 is a view illustrating processes of the step of forming the insulation layer according to the second embodiment of the present invention.

As illustrated in FIGS. 7, 12, and 13, after Step S330 of forming the metal electrode layer above the adhesion-performed upper substrate, Step S340 of forming the insulation layer on the metal electrode layer can be performed.

Besides, in Step S340 of forming the insulation layer on the metal electrode layer, first, Step S341 of forming a third Parylene layer by applying Parylene on the metal electrode layer can be performed.

After Step S341 of forming the third Parylene layer by applying Parylene on the metal electrode layer, a third Parylene layer 370a can be formed on the metal electrode layer 350b. Specifically, the metal electrode layer 350b is subjected to the wet etching to form a preset pattern. As illustrated in (k) of FIG. 13, the third Parylene layer 370a can be formed by applying Parylene to fill a space formed according to the pattern of the metal electrode layer 350b and cover the metal electrode layer 350b.

After Step S341 of forming the third Parylene layer by applying Parylene on the metal electrode layer, Step S342 of forming third masking patterns over the third Parylene layer can be performed.

In Step S342 of forming the third masking patterns over the third Parylene layer, third masking patterns 380 can be formed over the third Parylene layer 370a. As illustrated in (1) of FIG. 13, the third masking patterns 380 can be formed into preset patterns such that the third Parylene layer 370a can form an insulation layer 370b.

After Step S342 of forming the third masking patterns over the third Parylene layer, Step S343 of forming the insulation layer by irradiating plasma to the third Parylene layer with the third masking patterns and etching the third Parylene layer according to pattern shapes of the third masking patterns can be performed.

In Step S343 of forming the insulation layer by irradiating plasma to the third Parylene layer with the third masking patterns and etching the third Parylene layer according to the pattern shapes of the third masking patterns, the insulation layer 370b can be formed by etching the third Parylene layer 370a according to the pattern shapes of the third masking patterns 380 by the plasma with which irradiation is performed toward the third Parylene layer with the third masking patterns 380, as illustrated in (m) of FIG. 13.

The insulation layer 370b provided as described above can be subjected to patterning over a part of the metal electrode layer 350b such that the part of the metal electrode layer 350b can come into contact with the biological tissue. In other words, the insulation layer 370b can perform an insulating function with respect to the metal electrode layer 350b.

In addition, when the metal electrode layer 350b comes into contact with the biological tissue, the insulation layer 370b can reduce stress applied to the metal electrode layer 350b.

Besides, the plasma with which the irradiation is performed to etch the third Parylene layer 370a can be O2 plasma; however, the plasma is not limited thereto.

After Step S343 of forming the insulation layer by irradiating plasma to the third Parylene layer with the third masking patterns and etching the third Parylene layer according to the pattern shapes of the third masking patterns, Step S344 of removing the third masking patterns can be performed, as illustrated in (n) of FIG. 13.

After Step S340 of forming the insulation layer on the metal electrode layer, Step S350 of removing a carrier substrate under the lower substrate and injecting a drug can be performed.

In Step S350 of removing the carrier substrate under the lower substrate and injecting a drug, first, the carrier substrate 311 can be removed, as illustrated in (o) of FIG. 13.

Subsequently, as illustrated in (p) of FIG. 13, a drug can be injected into a channel formed in the upper substrate 320 and the lower substrate 310 such that the injected drug can be delivered to a biological tissue.

The drug delivery device 300 according to the second embodiment provided as described above can not only deliver a drug to a biological tissue but also measure an electrical signal of the biological tissue or apply electrical stimulation to the biological tissue.

Figure 14:
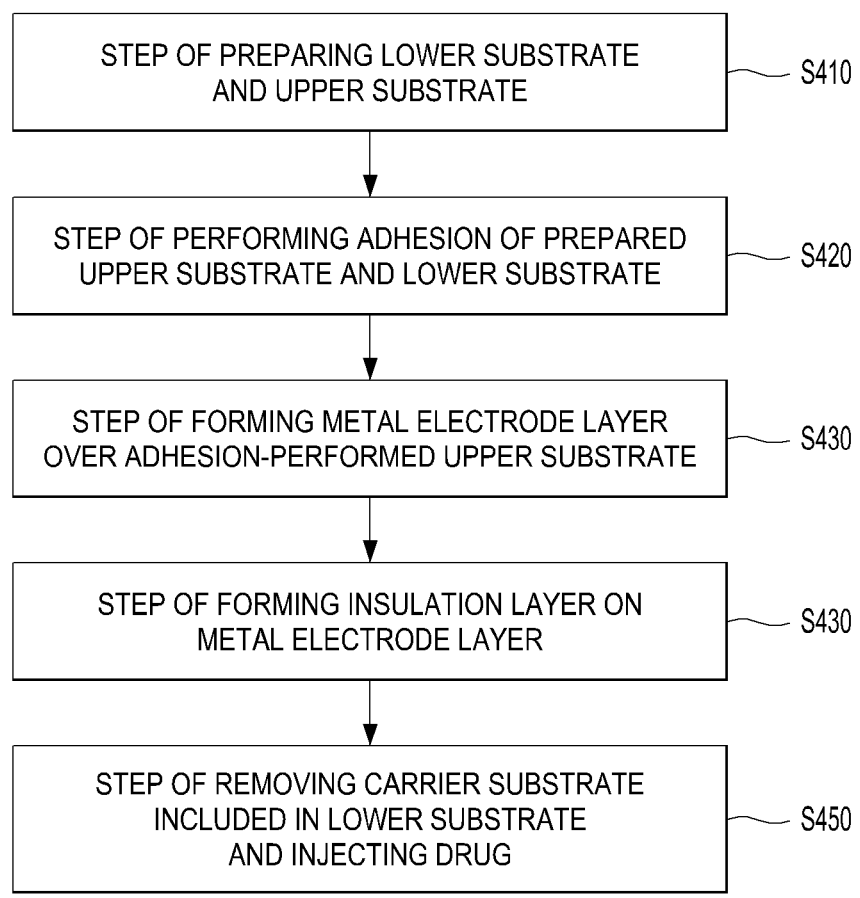
FIG. 14 is a flowchart of a method for manufacturing the drug delivery device according to the third embodiment of the present invention.
Figure 15:
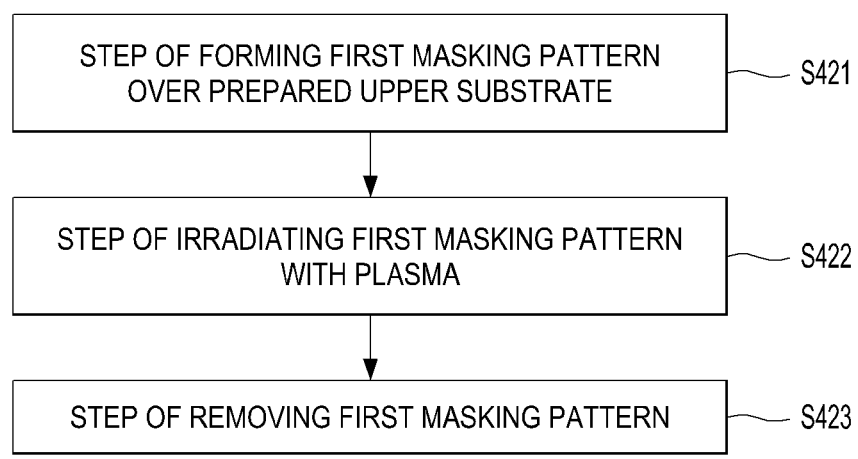
FIG. 15 is a flowchart of a step of performing adhesion according to the third embodiment of the present invention.
Figure 16:
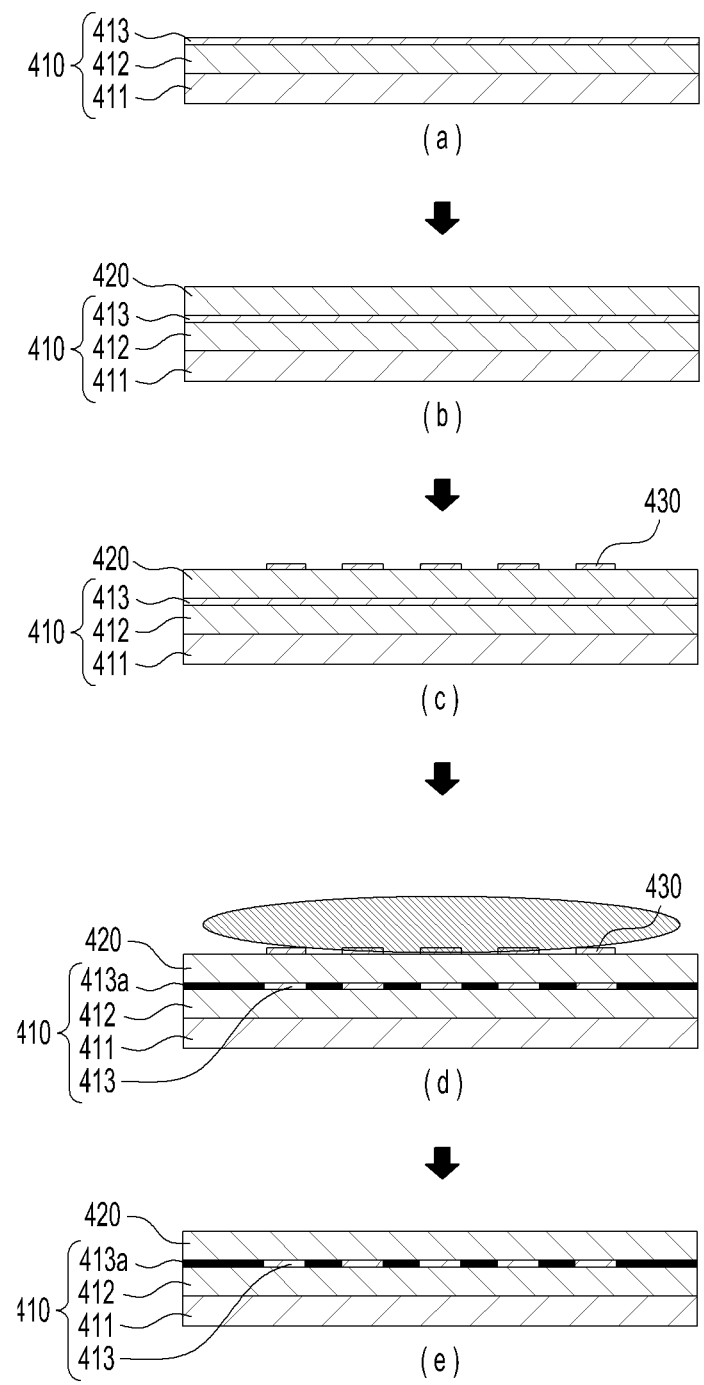
FIG. 16 is a view illustrating processes of a step of performing preparation and the step of performing the adhesion according to the third embodiment of the present invention.

FIG. 14 is a flowchart of a method for manufacturing the drug delivery device according to the third embodiment of the present invention, FIG. 15 is a flowchart of a step of performing adhesion according to the third embodiment of the present invention, and FIG. 16 is a view illustrating processes of a step of performing preparation and the step of performing the adhesion according to the third embodiment of the present invention.

As illustrated in FIGS. 14 to 16, in the method for manufacturing a drug delivery device 400 according to the third embodiment, first, Step S410 of preparing a lower substrate and an upper substrate can be performed.

In Step S410 of preparing the lower substrate and the upper substrate, as illustrated in (a) of FIG. 16, first, the lower substrate 410 can be provided to be prepared by forming a first polydimethylsiloxane (PDMS) spin-coating layer 412 over a carrier substrate 411 and forming a first Parylene layer 413 by applying Parylene over the first PDMS spin-coating layer 412 so as to be coupled thereto.

As illustrated in (b) of FIG. 16, the upper substrate 420 can be provided to be prepared by forming a second PDMS spin-coating layer 420 over the first Parylene layer 413.

Here, the lower substrate 410 and the upper substrate 420 can be prepared simultaneously, or the upper substrate 420 can be prepared before the lower substrate 410.

In addition, the lower substrate 410 and the upper substrate 420 correspond to the substrate unit 110 of the drug delivery device 100.

After Step S410 of preparing the lower substrate and the upper substrate, Step S420 of performing selective adhesion between the prepared upper substrate and lower substrate can be performed.

After Step S420 of performing the selective adhesion between the prepared upper substrate and lower substrate, first, Step S421 of forming first masking patterns over the prepared upper substrate is performed.

In Step S421 of forming the first masking patterns over the prepared upper substrate, the first masking patterns 430 can be formed to have pattern shapes at parts at which the upper substrate 420 and the lower substrate 410 are not joined to each other, as illustrated in (c) of FIG. 16.

In other words, when the upper substrate 420 and the lower substrate 410 adhere to each other, the adhering positions can be determined depending on the pattern shapes of the first masking patterns 430.

Besides, a plurality of the first masking patterns 430 according to the third embodiment can be provided separately from each other. Here, the first masking patterns 430 can be provided to have a size corresponding to a size of discharge voids to be formed.

As an example, the first masking patterns 430 can be provided to be arranged in a plurality of rows and columns at positions at which the discharge voids are to be subsequently formed.

After Step S421 of forming the first masking patterns over the prepared upper substrate, Step S422 of irradiating plasma to the substrate with the first masking patterns can be performed.

In Step S422 of irradiating plasma to the substrate with the first masking patterns, the plasma with which irradiation is performed toward the upper substrate with the first masking patterns 430 enables the first Parylene layer 413 positioned at an outer side of the first masking patterns 430 to adhere to the upper substrate 420, as illustrated in (d) of FIG. 16.

In other words, the plasma with which the irradiation is performed toward the upper substrate with the first Parylene layer 413 can heat parts which are not blocked by the first masking patterns 430 such that the upper substrate 420 and the lower substrate 410 adhere to each other.

In addition, the plasma can be $N_2/O_2$ plasma; however, the plasma is not limited thereto.

In Step S422 of irradiating plasma to the substrate with the first masking patterns, the discharge voids can be formed by putting and melting polyethylene glycol (PEG) at the positions of the upper substrate 420 made of PDMS at which the discharge voids are formed, performing the etching using the plasma, and initiating a crack in a surface of the upper substrate 420.

After Step S422 of irradiating plasma to the substrate with the first masking patterns, Step S423 of removing the first masking patterns can be performed, as illustrated in (e) of FIG. 16.

Figure 17:
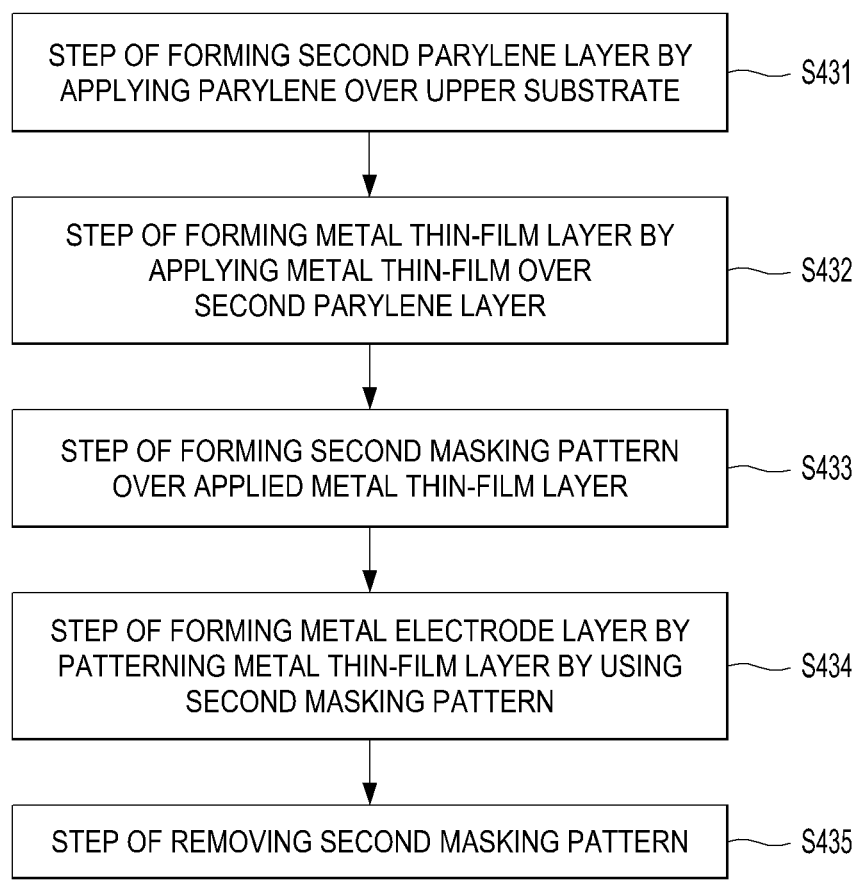
FIG. 17 is a flowchart of a step of forming a metal electrode layer according to the third embodiment of the present invention.
Figure 18:
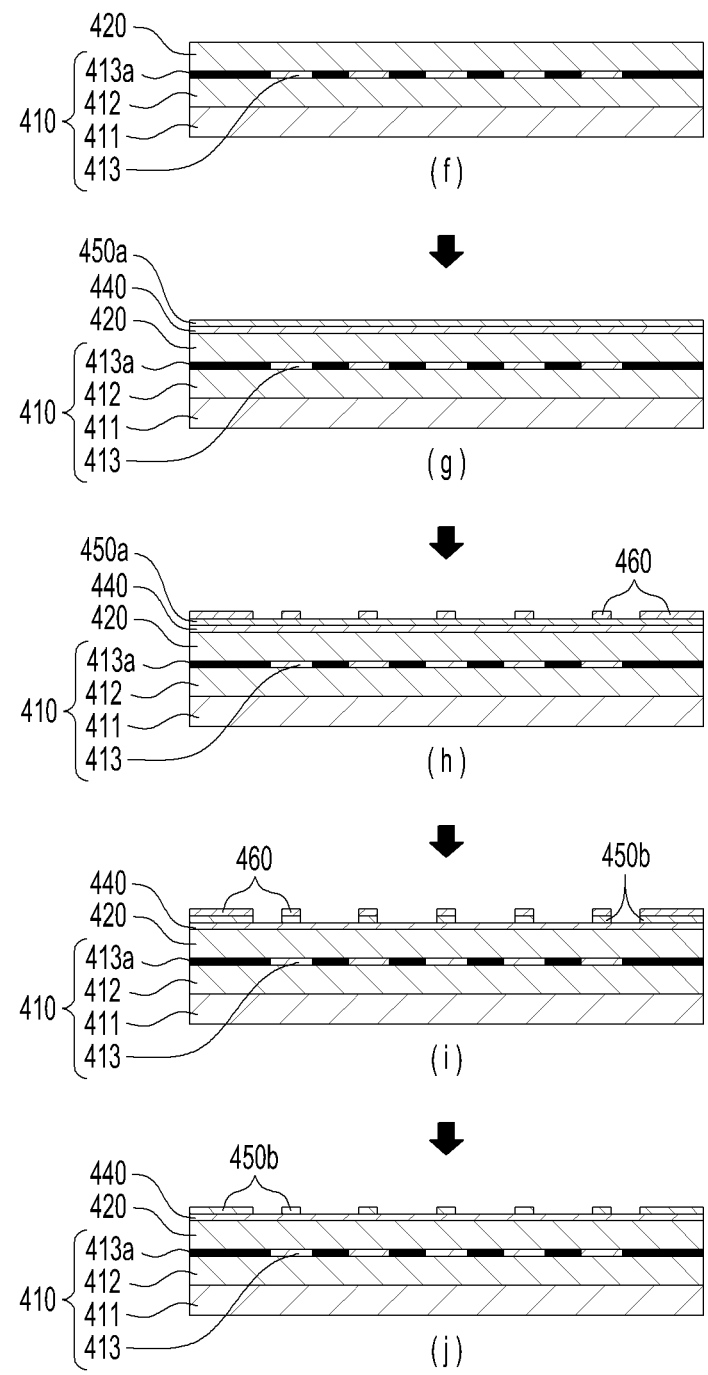
FIG. 18 is a view illustrating processes of the step of forming the metal electrode layer according to the third embodiment of the present invention.

FIG. 17 is a flowchart of a step of forming a metal electrode layer according to the third embodiment of the present invention, and FIG. 18 is a view illustrating processes of the step of forming the metal electrode layer according to the third embodiment of the present invention.

As illustrated in FIGS. 14, 17, and 18, after Step S420 of performing the selective adhesion between the prepared upper substrate and lower substrate, Step S430 of forming the metal electrode layer above the adhesion-performed upper substrate can be performed.

Besides, in Step S430 of forming the metal electrode layer above the adhesion-performed upper substrate, first, Step S431 of forming a second Parylene layer by applying Parylene over the upper substrate can be performed.

In Step S431 of forming the second Parylene layer by applying Parylene over the upper substrate, a second Parylene layer 440 can be formed by applying Parylene over the upper substrate 410, the Parylene being provided for applying a metal electrode, as illustrated in (f) of FIG. 18.

After Step S431 of forming the second Parylene layer by applying Parylene over the upper substrate, Step S432 of forming a metal thin-film layer by applying a metal thin-film over the second Parylene layer can be performed.

In Step S432 of forming the metal thin-film layer by applying the metal thin-film over the second Parylene layer, the metal thin-film is applied over the second Parylene layer 440, and thereby a metal thin-film layer 450*a* can be formed, as illustrated in (g) of FIG. 18.

Here, the metal thin-film of the metal thin-film layer 450*a* can contain Cr, Ti, Au, Pt, or the like.

In addition, when the metal thin-film is applied to form the metal thin-film layer 450*a*, a sputter and an evaporator can be used.

After Step S432 of forming the metal thin-film layer by applying the metal thin-film over the second Parylene layer, Step S433 of forming second masking patterns over the applied metal thin-film can be performed.

In Step S433 of forming the second masking patterns over the applied metal thin-film, second masking patterns 460 can be formed over the metal thin-film layer 450*a*, as illustrated in (h) of FIG. 18.

The second masking patterns 460 can be provided to form a metal electrode layer 450*b* by patterning the metal thin-film layer 450*a*, and thus the second masking patterns 460 can be provided to have pattern shapes corresponding to a preset shape of the metal electrode layer 450*b*.

In particular, in Step S433 of forming the second masking patterns over the applied metal thin-film, a plurality of the second masking patterns 460 can be provided separately from each other to be positioned above the first Parylene layer 413 which does not adhere to the upper substrate 420.

In other words, the second masking patterns 460 can be provided to be positioned above the first Parylene layer 413 at which an adhesive layer 413*a* is not formed. Besides, the second masking patterns 460 can be formed to have a diameter smaller than that of the first Parylene layer 413 which does not adhere to the upper substrate 420.

After Step S433 of forming the second masking patterns over the applied metal thin-film, Step S434 of forming the metal electrode layer by patterning the metal thin-film layer by using the second masking patterns can be performed.

In Step S434 of forming the metal electrode layer by patterning the metal thin-film layer by using the second masking patterns, the metal electrode layer 450*b* can be formed by patterning the metal thin-film layer 450*a* according to the second masking patterns 460. More specifically, as illustrated in (i) of FIG. 18, in Step S434 of forming the metal electrode layer by patterning the metal thin-film layer by using the second masking patterns, the metal electrode layer 450*b* can be formed by etching and patterning the metal thin-film layer 450*a* according to the pattern shapes of the second masking patterns 460 through a wet etching process.

The wet etching process is performed on the metal thin-film layer 450*a* in a state where the second masking patterns 460 are settled over the metal thin-film layer, and thus etching of the metal thin-film layer can be rapidly and accurately performed at low costs.

After Step S434 of forming the metal electrode layer by patterning the metal thin-film layer by using the second masking patterns, Step S435 of removing the second masking patterns can be performed, as illustrated in (j) of FIG. 18.

The metal electrode layer 450*b* provided as described above corresponds to the measurement unit 120 of the drug delivery device 100.

Figure 19:
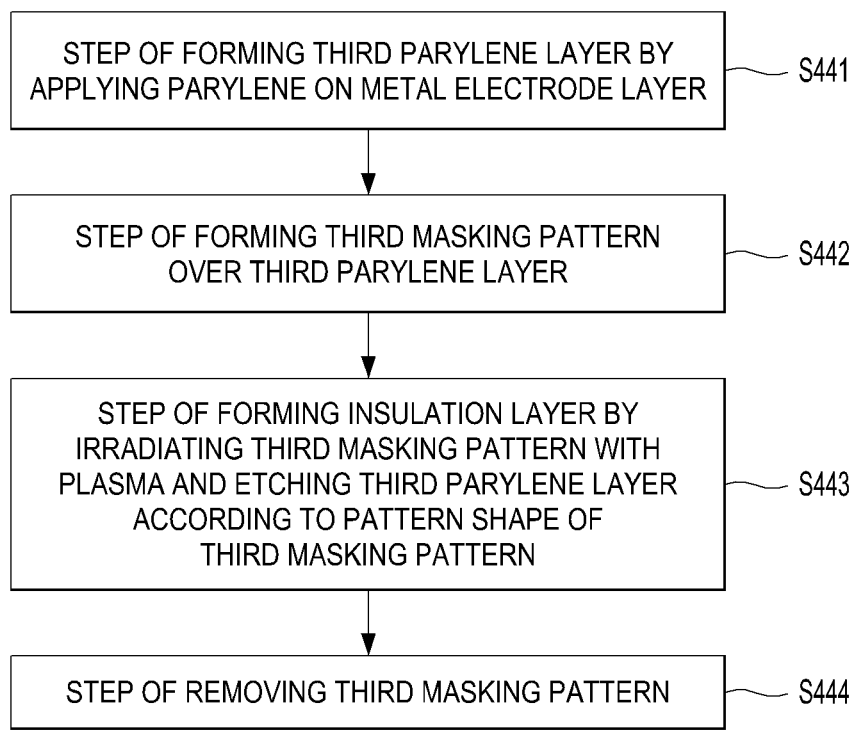
FIG. 19 is a flowchart of a step of forming an insulation layer according to the third embodiment of the present invention.
Figure 20:
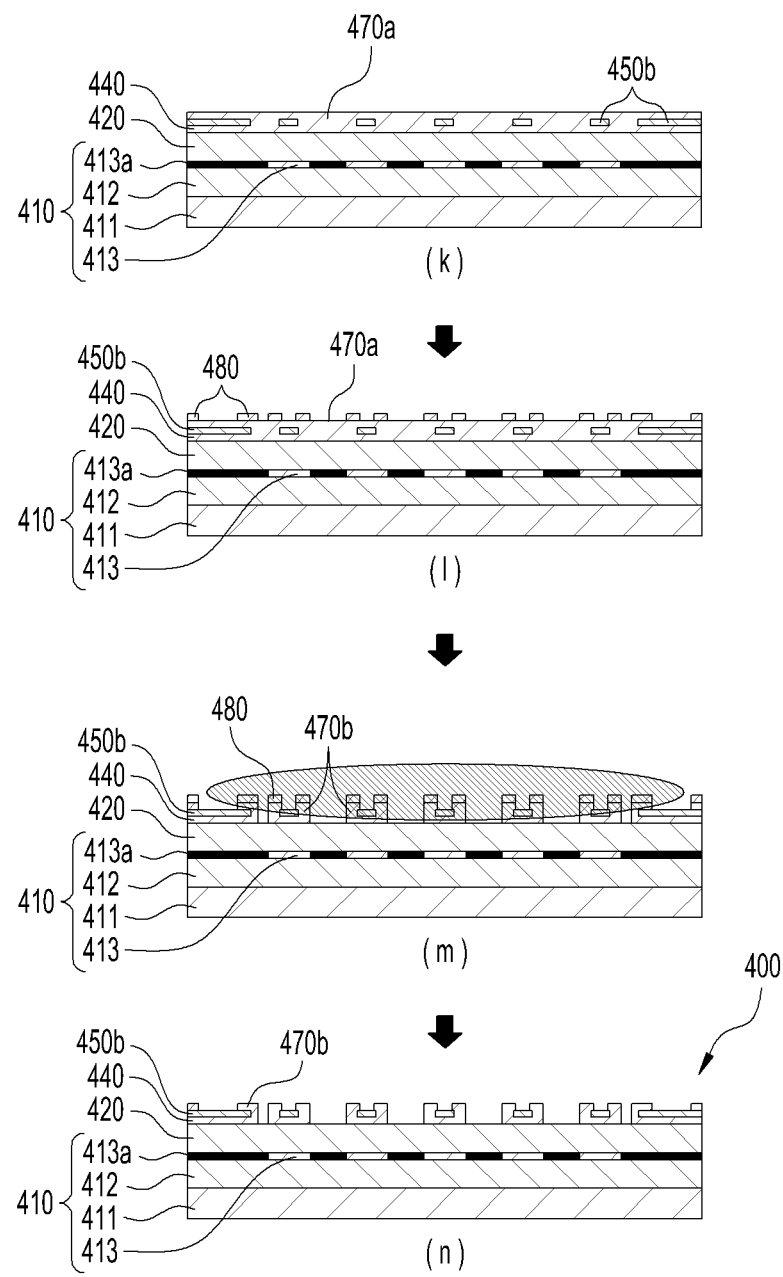
FIG. 20 is a view illustrating processes of the step of forming the insulation layer according to the third embodiment of the present invention.

FIG. 19 is a flowchart of a step of forming an insulation layer according to the third embodiment of the present invention, and FIG. 20 is a view illustrating processes of the step of forming the insulation layer according to the third embodiment of the present invention.

As illustrated in FIGS. 14, 19, and 20, after Step S430 of forming the metal electrode layer above the adhesion-performed upper substrate, Step S440 of forming the insulation layer on the metal electrode layer can be performed.

In Step S440 of forming the insulation layer on the metal electrode layer, first, Step S441 of forming the third Parylene layer by applying Parylene on the metal electrode layer can be performed.

After Step S441 of forming the third Parylene layer by applying Parylene on the metal electrode layer, a third Parylene layer 470a can be formed on the metal electrode layer 450b. Specifically, the metal electrode layer 450b is subjected to the wet etching to form a preset pattern. As illustrated in (k) of FIG. 20, the third Parylene layer 470a can be formed by applying Parylene to fill a space formed according to the pattern of the metal electrode layer 450b and cover the metal electrode layer 450b.

After Step S441 of forming the third Parylene layer by applying Parylene on the metal electrode layer, Step S442 of forming the third masking patterns over the third Parylene layer can be performed.

In Step S442 of forming the third masking patterns over the third Parylene layer, third masking patterns 480 can be formed over the third Parylene layer 470a. As illustrated in (l) of FIG. 20, the third masking patterns 480 can be formed into preset patterns such that the third Parylene layer 470a can form an insulation layer 470b.

In particular, in the third embodiment, the third masking patterns 480 can be formed over the third Parylene layer 470a and formed at positions corresponding to both end portions of the metal electrode layer 450b.

After Step S442 of forming the third masking patterns over the third Parylene layer, Step S443 of forming the insulation layer by irradiating plasma to the third Parylene layer with the third masking patterns and etching the third Parylene layer according to pattern shapes of the third masking patterns can be performed.

In Step S443 of forming the insulation layer by irradiating plasma to the third Parylene layer with the third masking patterns and etching the third Parylene layer according to the pattern shapes of the third masking patterns, the insulation layer 470b can be formed by etching the third Parylene layer 470a according to the pattern shapes of the third masking patterns 480 by the plasma with which irradiation is performed toward The third Parylene layer with the third masking patterns 480, as illustrated in (m) of FIG. 20.

The insulation layer 470b provided as described above can be subjected to patterning over a part of the metal electrode layer 450b such that the part of the metal electrode layer 450b can come into contact with the biological tissue. In other words, the insulation layer 470b can perform an insulating function with respect to the metal electrode layer 450b.

In addition, when the metal electrode layer 450b comes into contact with the biological tissue, the insulation layer 470b can reduce stress applied to the metal electrode layer 450b.

Besides, the plasma with which the irradiation is performed to etch the third Parylene layer 470a can be O2 plasma; however, the plasma is not limited thereto.

After Step S443 of forming the insulation layer by irradiating plasma to the third Parylene layer with the third masking patterns and etching the third Parylene layer according to the pattern shapes of the third masking patterns, Step S444 of removing the third masking patterns can be performed, as illustrated in (n) of FIG. 20.

After Step S440 of forming the insulation layer on the metal electrode layer, Step S450 of removing a carrier substrate under the lower substrate and injecting a drug can be performed.

In Step S450 of removing the carrier substrate under the lower substrate and injecting a drug, first, the carrier substrate 411 can be removed, as illustrated in (o) of FIG. 20.

Subsequently, as illustrated in (p) of FIG. 20, a drug can be injected into a channel formed in the upper substrate 420 and the lower substrate 410 such that the injected drug can be delivered to a biological tissue.

Figure 21:
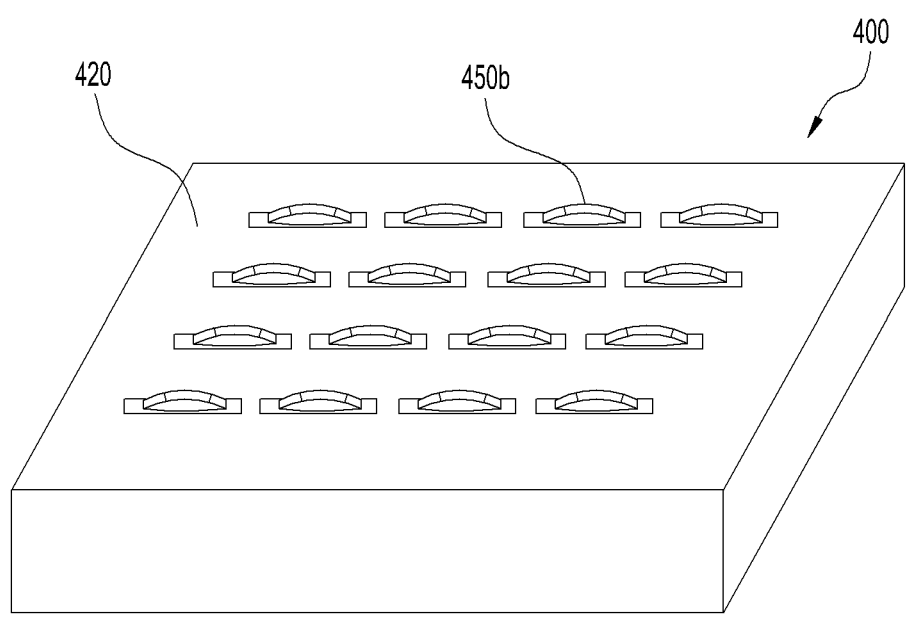
FIG. 21 is a view illustrating a drug delivery device manufactured in accordance with the method for manufacturing the drug delivery device according to the third embodiment of the present invention.

FIG. 21 is a view illustrating a drug delivery device manufactured in accordance with the method for manufacturing the drug delivery device according to the third embodiment of the present invention.

With reference to FIG. 21, the drug delivery device 400 according to the third embodiment can not only deliver a drug to a biological tissue but also measure an electrical signal of the biological tissue or apply electrical stimulation to the biological tissue.

Besides, the drug delivery device 400 according to the third embodiment can control the types, the injection rate, and the concentration of drugs for each position in various manners by adjusting the porosity of the discharge voids and the void size.

The description of the present invention described above is provided as an example, and a person of ordinary skill in the art to which the present invention belongs can understand that it is possible to easily modify the present invention to another embodiment without altering the technical idea or an essential feature of the present invention. Therefore, the embodiments described above need to be understood as exemplified examples in every aspect and not as examples to limit the present invention. For example, configurational elements described in a singular form can be realized in a distributed manner. Similarly, the configurational elements described in the distributed manner may be realized in a combined manner.

The scope of the present invention needs to be represented by the claims to be described below, and meaning and the scope of the claims and every modification or modified embodiment derived from an equivalent concept of the claims need to be construed to be included in the scope of the present invention.

REFERENCE SIGNS LIST

10 DRUG DELIVERY DEVICE
11 SUBSTRATE UNIT
12 DISCHARGE VOID
100 DRUG DELIVERY DEVICE
110 SUBSTRATE UNIT
111 INSERTION PORTION
112 CHIP INSTALLED PORTION
120 MEASUREMENT UNIT
121 CABLE
122 MEASUREMENT PORTION
130 CIRCUIT UNIT
200, 300, 400 DRUG DELIVERY DEVICE
210, 310, 410 LOWER SUBSTRATE
211, 311, 411 CARRIER SUBSTRATE
212, 312, 412 FIRST PDMS SPIN-COATING LAYER
213, 313, 413 FIRST PARYLENE LAYER
213a, 313a, 413a ADHESIVE LAYER
220, 320, 420 UPPER SUBSTRATE
230, 330, 430 FIRST MASKING PATTERN
240, 340, 440 SECOND PARYLENE LAYER
250a, 350a, 450a METAL THIN-FILM LAYER
250b, 350b, 450b METAL ELECTRODE LAYER
260, 360, 460 SECOND MASKING PATTERN
270a, 370a, 470a THIRD PARYLENE LAYER
270b, 370b, 470b INSULATION LAYER
280, 380, 480 THIRD MASKING PATTERN
290 INJECTION PORT
H THROUGH-HOLE

The invention claimed is:

1. A drug delivery device comprising:
a substrate unit that is capable of being inserted into a human body and has a porous insertion portion having a plurality of discharge voids spaced apart from each other,
wherein the insertion portion is provided to be deformable to match a shape of a biological tissue, and while the insertion portion expands and contracts, a drug is injected into and discharged from the plurality of discharge voids of the insertion portion,
wherein the insertion portion is provided with a plurality of pores through which the drug is delivered, and the pores are distributed right on the plurality of discharge voids and only located on a first side wall of the insertion portion,
wherein the insertion portion is provided to deliver the drug from the plurality of discharge voids to the biological tissue through the pores in a state that the first side wall of the insertion portion is in close contact with the biological tissue, thus the drug discharged from each of the plurality of discharge voids is delivered to the biological tissue without mixing,
wherein the plurality of discharge voids are provided to allow drugs of the same type and concentration to be injected into the plural discharge voids, or drugs, of which one or both of type and concentration are different from each other, to be injected into the plurality of discharge voids.

2. The drug delivery device according to claim 1, further comprising:
a measurement unit that is provided at one or both surfaces of the substrate unit.

3. The drug delivery device according to claim 2, further comprising:
a circuit unit that is coupled to the substrate unit and has an IC chip connected to the measurement unit.

4. The drug delivery device according to claim 3,
wherein the substrate unit further has a chip installed portion that is provided to be extended from the insertion portion and is coupled to the circuit unit.

5. The drug delivery device according to claim 3,
wherein the measurement unit has
one or more cables provided to be extended from the IC chip to the insertion portion, and
one or more measurement portions that are positioned on the insertion portion and are provided separately from each other at each of the cables.

6. The drug delivery device according to claim 5,
wherein the one or more measurement portions include one or more of sensors and electrodes and are provided to be able to measure an electrical signal of the biological tissue and electrically stimulate the biological tissue.

7. The drug delivery device according to claim 5,
wherein the plurality of discharge voids are provided to be positioned below the one or more measurement portions.

* * * * *